(12) United States Patent
Cohen

(10) Patent No.: US 7,286,871 B2
(45) Date of Patent: Oct. 23, 2007

(54) METHOD AND APPARATUS FOR REDUCING CONTAMINATION OF AN ELECTRICAL SIGNAL

(75) Inventor: Mark S. Cohen, Calabasas, CA (US)

(73) Assignee: The Regents of the University of California, Oakland, CA (US)

( * ) Notice: Subject to any disclaimer, the term of this patent is extended or adjusted under 35 U.S.C. 154(b) by 1046 days.

(21) Appl. No.: 10/344,776

(22) PCT Filed: Aug. 15, 2001

(86) PCT No.: PCT/US01/25480

§ 371 (c)(1),
(2), (4) Date: Feb. 18, 2003

(87) PCT Pub. No.: WO02/13689

PCT Pub. Date: Feb. 21, 2002

(65) Prior Publication Data

US 2004/0097802 A1    May 20, 2004

Related U.S. Application Data

(60) Provisional application No. 60/267,337, filed on Feb. 7, 2001, provisional application No. 60/225,389, filed on Aug. 15, 2000.

(51) Int. Cl.
*A61B 5/04* (2006.01)
(52) U.S. Cl. ............... 600/544; 600/300; 600/411; 702/69; 702/191
(58) Field of Classification Search ........... 702/190, 702/191, 193, 19, 69, 111; 600/407–435, 600/544–547, 509, 300, 301; 324/613, 620
See application file for complete search history.

(56) References Cited

U.S. PATENT DOCUMENTS 4,781,200 A * 11/1988 Baker ................. 600/483

(Continued)

FOREIGN PATENT DOCUMENTS

WO    WO 94/27497 A1    12/1994

OTHER PUBLICATIONS

Allen, P.J., et al., "A Method for Removing Imaging Artifact from Continuous EEG Recorded during Functional MRI", in A. W. Toga, et al. (eds.) *NeuroImage*, vol. 12, No. 2, Aug. 2000, pp. 230-239.

(Continued)

*Primary Examiner*—Charles A. Marmor, II
*Assistant Examiner*—Karen E Toth
(74) *Attorney, Agent, or Firm*—candy & lortz LLP; Karen S. Canady

(57) ABSTRACT

The method of reducing contamination of electrical signals recorded in the presence of repeated interference contamination comprises obtaining an electrical signal recorded in the presence of a contaminating signal, and detecting a timing signal that occurs at a fixed time point during the electrical signal relative to the onset of the contaminating signal. The electrical signal is digitized, wherein the digitizing begins with the timing signal. A plurality of digitized electrical signals is analyzed, wherein the electrical signals are synchronized with respect to the timing signal, to obtain an estimated contaminating signal that is subtracted from the digitized electrical signal. This method can be used with electrophysiological signals, such as EEG, ECG, EMG and galvanic skin response, and for elimination of noise associated with concurrently used methods such as MRI. The method of noise reduction is applicable to recordings of other electrical signals, including audio recordings.

34 Claims, 16 Drawing Sheets

U.S. PATENT DOCUMENTS

| | | | |
|---|---|---|---|
| 4,887,609 A | | 12/1989 | Cole, Jr. |
| 5,217,010 A | | 6/1993 | Tsitlik et al. |
| 5,230,344 A | | 7/1993 | Ozdamar et al. |
| 5,341,811 A | * | 8/1994 | Cano .......................... 600/508 |
| 5,436,564 A | | 7/1995 | Kreger et al. |
| 5,445,162 A | | 8/1995 | Ives |
| 5,482,036 A | * | 1/1996 | Diab et al. .................. 600/364 |
| 5,513,649 A | | 5/1996 | Gevins et al. |
| 5,532,944 A | * | 7/1996 | Battista ......................... 708/3 |
| 5,546,332 A | * | 8/1996 | Strobach ..................... 702/190 |
| 5,704,365 A | * | 1/1998 | Albrecht et al. ............. 600/515 |
| 5,742,900 A | * | 4/1998 | Arnstein et al. ............. 455/296 |
| 5,748,507 A | * | 5/1998 | Abatzoglou et al. ........... 702/76 |
| 5,966,684 A | * | 10/1999 | Richardson et al. ........ 702/191 |
| 6,181,961 B1 | * | 1/2001 | Prass .......................... 600/547 |
| 6,520,283 B2 | * | 2/2003 | Kemeny ..................... 181/207 |
| 7,038,601 B2 | * | 5/2006 | Uutela et al. ............... 341/118 |
| 2004/0106876 A1 | * | 6/2004 | Schmid et al. .............. 600/509 |
| 2005/0197586 A1 | * | 9/2005 | Pearlman .................... 600/509 |
| 2005/0277826 A1 | * | 12/2005 | Dunseath .................... 600/410 |

OTHER PUBLICATIONS

Archer, J., et al., "Spike triggered fMRI: a technique for understanding the aetiology of epileptifrm activity", in A. W. Toga, et al. (eds.) *NeuroImage*, vol. 13, No. 6, Jun. 2001, Seventh Annual Meeting of the Organization for Human Brain Mapping, Brighton, UK, p. S768.

Bonmassar, G., et al., "Simultaneous EEG/fMRI Recordings: 64 Channel VEPs and 3T fMRI", in A. W. Toga et al. (eds.) *NeuroImage*, vol. 9, No. 6, Jun. 1999, p. S254.

Goldman, Robin I., et al., "Simultaneous EEG and fMRI of the alpha rhythm", in *Brain Imaging, NeuroReport*, vol. 13, No. 18, Dec. 20, 2002, pp. 2487-2492.

Hoffmann, A., et al., "Electroencephalography During Functional Echo-Planar Imaging: Detection of Epileptic Spikes Using Post-processing Methods", in F. W. Wehrli, et al. (eds.)*Magnetic Resonance in Medicine*, vol. 44, No. 5, Nov. 2000, pp. 791-798.

Krakow, K. et al., "Methodology: EEG-correlated fMRI", in T. R. Henry, et al. (eds.) *Advances In Neurology*, vol. 83, Functional Imaging in the Epilepsies,, 2000, pp. 187-201.

Krakow, K., et al., "Spatio-temporal imaging of focal interictal epileptiform activity using EEG-triggered functional MRI", in *Epileptic Disorders*, International Epilepsy Journal With Video Sequences, vol. 3, No. 2, Jun. 2001, pp. 67-73.

Krakow, K., et al., "Functional MRI Activation of Individual Interictal Epileptiform Spikes", in A. W. Toga et al. (eds.) *NeuroImage*, vol. 13, No. 3, Mar. 2001, pp. 502-505.

Schomer, D.L., "EEG-Linked Functional Magnetic Resonance Imaging in Epilepsy and Cognitive Neurophysiology", in *Journal of Clinical Neurophysiology*, vol. 17, No. 1, Jan. 2000, pp. 43-58.

Warach, S., et al., "EEG-triggered echo-planar functional MRI in epilepsy", in R. B. Daroff, et al. (eds.) *Neurology*, vol. 47, No. 1, Jul. 1996, pp. 89-93.

Lemieux, L., et al., "Methodological Issues in EEG-correlated Functional MRI Experiments", International Journal of Bioelectromagnetism (I)BEM), No. 1, vol. 1, 1999, pp. 1-13.

Krakow, K., et al., "EEG recording during fMRI experiments: image quality", Human Brain Mapping 10(1): 10-5, May 2000.

Allen, P.J., et al., "Identification of EEG events in the MR scanner: the problem of pulse artifact and a method for its subtraction", Neuroimage 8(3): 229-39, 1998.

Cohen, M.S., et al., "Localization of brain function using magnetic resonance imaging", Trends in Neuroscience; 17(7): 268-77, 1994.

Ives, J.R., et al., "Monitoring the patient's EEG during echo planar MRI", Electroencephalography & Clinical Neurophysiology. 87(6): 417-20, Dec. 1993.

Huang-Hellinger, et al., "Simultaneous Functional Magnetic Resonance Imaging and Electrophysiological Recording", Human Brain Mapping 3(1):13-23, 1995.

* cited by examiner

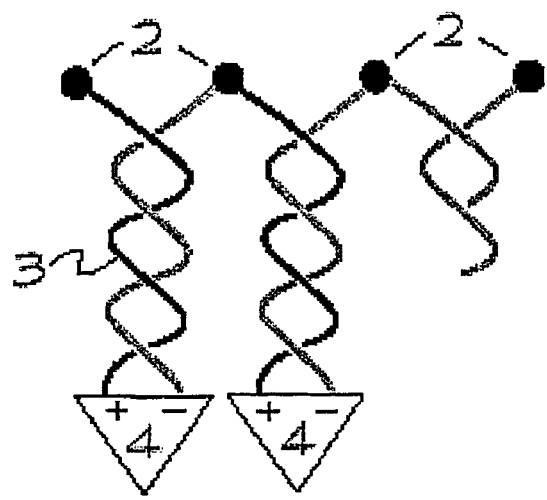
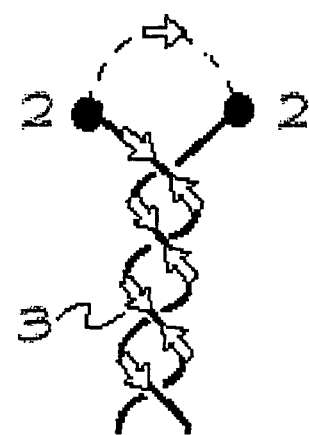
Figure 2A Figure 2B
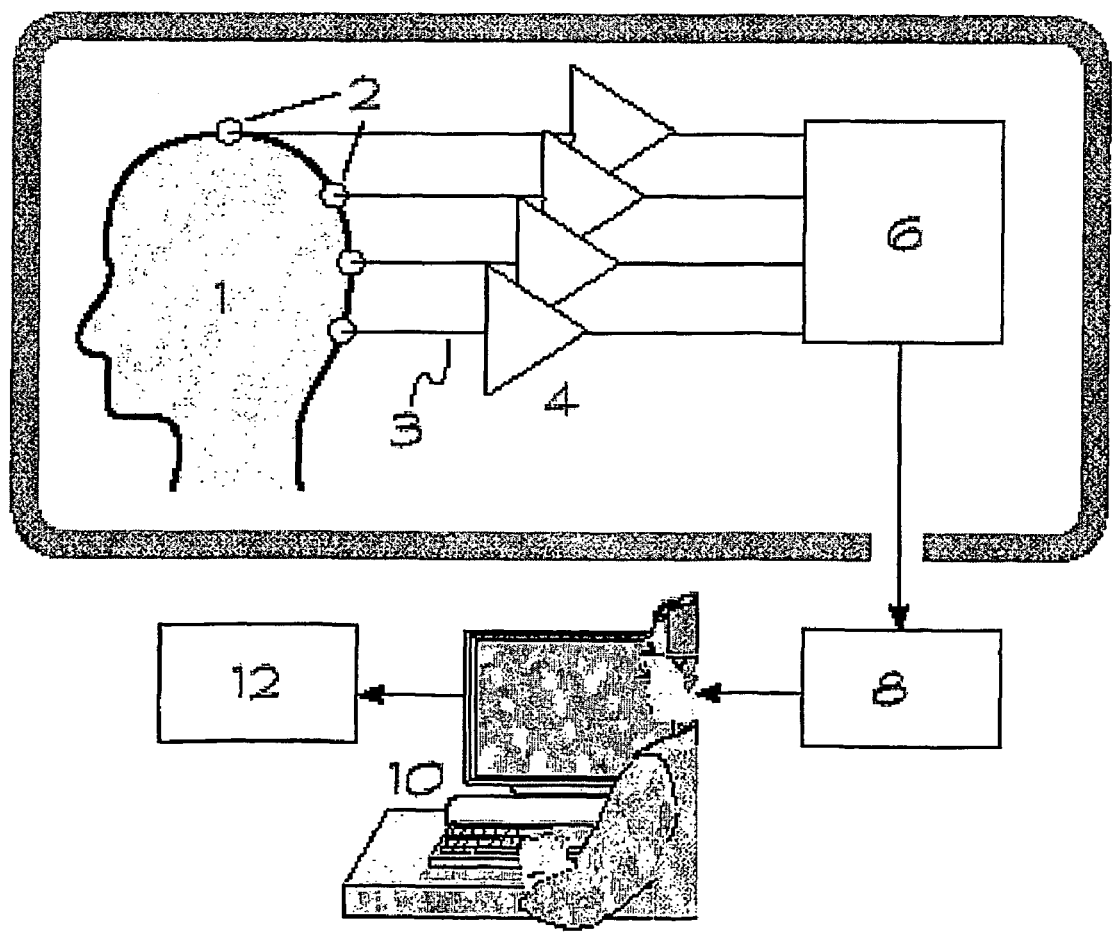
Figure 3

METHOD AND APPARATUS FOR REDUCING CONTAMINATION OF AN ELECTRICAL SIGNAL

This application claims the benefit of U.S. provisional patent application numbers 60/225,389, filed Aug. 15, 2000, and 60/267,337, filed Feb. 7, 2001, the entire contents of each of which are incorporated herein by reference. Throughout this application, various publications are referenced. The contents of these references are incorporated by reference herein, in order to describe more fully the state of the art.

TECHNICAL FIELD OF THE INVENTION

This invention relates generally to methods and apparatus for signal processing and data collection that are particularly suited for minimizing artifacts and optimizing signal-to-noise in simultaneous recording of electroencephalographic (EEG) and Magnetic Resonance Imaging R signals, as well as other environments in which electrical signals are subject to repeated interference. The methods of the invention can be applied to other recordings containing repeated electrical interference, including eletromyelographic (EMG), electro-cardiographic (ECG) or galvanic skin resistance (GSR) signals recording during fMRI and audio recordings or transmissions in the presence of 60 Hz noise or electrical transients.

BACKGROUND OF THE INVENTION

Electroencephalography MEG) and functional MRI (fMRI) induce mutual artifacts when recorded concurrently. Electroencephalography (EEG) has been a key tool for study of the brain for decades. However, despite its multiple clinical and research uses, such as in epilepsy (Ebersole, 1997), sleep staging (Rechtschaffen & Kales, 1968) and psychophysiology, little is yet known about the underlying generators of EEG activity in humans. Functional MRI (fMRI) recorded in concert with EEG can provide a method for localizing these sources. By using the ERG signal as a reference for fMRI maps, concurrent EEG/fMRI opens a new avenue for investigating specific brain function. There remains a need for a system for simultaneous recording of EEG and fMRI, which can be used as a tool to localize sources of the EEG.

Simultaneous recording of EEG and fMRI has proven challenging. Time varying magnetic (B) fields induce an electromotive force (e.m.f.) in a wire loop perpendicular to the B field direction which, by Lenz's Law, is proportional to the cross sectional area of the wire loop and to the rate of change of the perpendicular magnetic field (dB/dt). When EEG leads are placed inside the MR scanner, the rapidly changing gradient fields and the radio-frequency A) pulses required for MRI may induce voltages that obscure the EEG signal (Huang-Hellinger, et al., 1995; Ives, Warach, Schmitt, Edelman, & Schomer, 1993). The induced e.m.f. yields currents that can cause heating of the electrodes and leads and potentially impart burns to the patient (Lemieux, Allen, Franconi, Symms, & Fish, 1997). Motion of the leads themselves within the static field of the magnet also induces an e.m.f.; even pulsatile motion related to heart beat yields ballistocardiographic artifact in the EEG that can be of roughly the same magnitude as the EEG signals themselves (Ives, Warach, Schmitt, Edelman, & Schomer, 1993; Muri, et al, 1998). Further, introduction of EEG equipment into the scanner potentially can disturb the homogeneity of the magnetic field and distort the resulting MR images.

In addition to the large artifacts in the EEG caused by high frequency gradient and RF pulses, the high pass filters of most EEG equipment lead to long signal recovery times once the MR acquisition has terminated (Krakow, et al., 1999). One method used to overcome these difficulties in studies of epilepsy has been to monitor the EEG in the absence of scanning while the patient is in the magnet and to then trigger functional scanning manually after identification of inter-ictal spikes in the EEG record (Krakow, et al., 1999; Seeck, et al., 1998; Warach, et al, 1996). Visual evoked potential has been studied using interleaved blocks of EEG and fMRI, where the same stimuli are presented in each block (Bonmassar, Anami, Ives, & Belliveau, 1999). In these methods, EEG and fMRI are acquired serially, resulting in protocol limitations and problems with data analysis. In the triggered method, relevant changes in the EEG can not be seen during functional scanning. Problems also exist with non-uniform MR image contrast, given that T1 saturation typically does not reach equilibrium until 3 to 4 TRs after initiation of the scan (depending on TR and effective flip angle). Most often this is handled by ignoring images acquired in the first 3-4 TRs, but this then leads to an inherent time delay in the functional scanning. This could be mitigated to some degree by using schemes that correct for the T1-related intensity differences based on the actual TR (DuBois & Cohen, 2000; Guimaraes, et al., 1998). In the interleaved method, in addition to the former confounds, the EEG and fMRI can not be compared directly.

SUMMARY OF THE INVENTION

To overcome the limitations in the prior art described above, and to overcome other limitations that will become apparent upon reading and understanding the present specification, the invention provides a method of reducing contamination of electrical signals recorded in the presence of repeated interference contamination. The method comprises obtaining an electrical signal wherein the electrical signal was recorded in the presence of a contaminating signal, and detecting a timing signal that occurs at a fixed time point during the electrical signal relative to the onset of the contaminating signal.

The method further comprises digitizing the electrical signal, wherein the digitizing begins with the timing signal A plurality of digitized electrical signals is then analyzed, wherein the electrical signals are synchronized with respect to the timing signal, to obtain an estimated contaminating signal The estimated contaminating signal is subtracted from the digitized electrical signal, thereby reducing contamination of the electrical signal In a preferred embodiment, the analysis to obtain the estimate of the contaminating signal comprises averaging the electrical signals. In some embodiments, the analysis to obtain the estimate of the contaminating signal comprises calculating a weighted average of the electrical signals. The estimate of the contaminating signal can be biased towards recent events, for example, by adding the nth electrical signal to a scalar multiple, w, of the prior estimate of the contaminating signal and dividing this first sum by a second sum obtained by adding the series $1+w^2+w^3+w^4 \ldots + \ldots w^n$. The estimate of the contaminating signal further can be multiplied by a scalar prior to the subtracting step.

The method is particularly suitable for electrical recordings which comprise an electrophysiological signal, such as an electroencephalographic recording, an electromyelographic recording, an electrocardiographic recording or a measure of galvanic skin resistance. The method is applicable as well to other types of electrical recordings, including audio recordings. In some embodiments, the interference comprises interference arising from inductively coupled magnetic fields. The interference can also comprise interference arising from alternating current (AC) line noise.

One advantageous feature of the method of the invention is that the digitizing can be performed at a sampling rate below the Nyquist rate for the contaminating signal. In one embodiment, the electrical signal obtained is passed through a low pass filter prior to the digitizing, at a frequency of approximately one half of the frequency at which the electrical signal is sampled. For example, the low pass filter may pass signal frequencies of less than about 200 Hz.

The method can be performed concurrently with Magnetic Resonance Imaging of the subject. In one embodiment, the electrical signal comprises an electrophysiological signal and the contaminating signal comprises gradient activity. Examples of a contaminating signal include radio frequency transmitter activity. In a preferred embodiment of the method, the digitizing is performed at a rate of about 200 to about 5000 samples per second. The digitizing can be performed at rates below 200 and above 5000 samples per second, with representative rates including 100, 250, 500, 1000, 2000, 3000, 4000 and 6000 samples per second.

The invention additionally provides a method of removing a DC offset from the electrical signal by analog subtraction prior to the digitizing. Preferably, the DC offset is measured and subtracted from the electrical signal using a difference amplifier. In one embodiment, the DC offset is measured by analog to digital conversion, and averaged over a time period long compared to the lowest frequencies of interest in the electrical signal An example of such a long time period is approximately 10 times longer than the lowest frequencies of interest in the electrical signal For example, where lowest frequencies of interest are approximately 3 Hz, the time period is about 30 seconds. In one embodiment, the analog subtraction comprises converting the averaged signal to an analog voltage and electrically subtracting the averaged signal from the electrical signal through differential amplification. In another embodiment, the DC offset is measured in an analog integrator having a time constant long compared with lowest frequencies of interest in the signal The method of the invention is useful for electrophysiological recordings, such as in an electroencephalogram that is recorded concurrently with magnetic resonance image acquisition. In a preferred embodiment, the electrophysiological recordings are used to inform interpretations of magnetic resonance images. The electrophysiological recordings can be used in a statistical analysis of change in intensity of the magnetic resonance signal The method can further comprise determining a correlation between change in intensity of the magnetic resonance signal and a feature of the electrophysiological recording. The correlation can be used to make statistical images, or image maps, that represent an association between the electrical signals and the intensity of the magnetic resonance signal intensity. In one embodiment, the feature of the electrophysiological recording comprises a time course of signal intensity change in defined frequency bands contained in the electrophysiological recording.

The defined frequency bands can be selected to correspond to standard ranges used for clinical interpretations of the electroencephalogram. Representative standard ranges are selected from the group consisting of from 0 to approximately 4 Hz (the Delta band), from approximately 4 to approximately 8 Hz (the Theta band), from approximately 8 to approximately 12 Hz (the Alpha band), from approximately 12 to approximately 30 Hz (the Beta band), and from approximately 30 Hz and greater (the Gamma band). Typically, the frequency bands in this context will not extend beyond 300 Hz. In one embodiment, the method further comprises convolving the time course of the electrophysiological signal with an estimate of the magnetic resonance hemodynamic impulse response function. In this embodiment, the time course of the electrophysiological signal is suitably conditioned to more accurately reflect the anticipated time course of the magnetic resonance signal change.

The invention additionally provides a method of reducing magnetic interference during electrophysiological recording from a subject by measuring an electrical potential difference between a pair of electrodes, wherein the pair of electrodes communicate with a differential amplifier via electrical connections, the method comprising twisting the electrical connections together, thereby reducing magnetic interference. Also provided is a method of reducing magnetic interference during electrophysiological recording from a subject by measuring an electrical potential difference between a pair of adjacent electrodes, wherein each electrode comprises two leads, the method comprising twisting each lead together with a lead of an adjacent electrode, thereby reducing magnetic interference. In one embodiment, the electrophysiological recording comprises an electroencephalographic recording. The method can be performed concurrently with Magnetic Resonance Imaging of the subject The invention further provides an apparatus for processing digitized electrical signals in the presence of a repeated contaminating signal The apparatus comprises a signal processor adapted to receive a recording of an electrical sign a detector adapted to detect a timing signal that occurs at a fixed time point during an electrical signal relative to the onset of a contaminating signal; a signal accumulator to contain the estimated contaminating signal; and a processor adapted to subtract averaged waveforms from an electrical signal. The signal accumulator can be, for example, a signal averager.

BRIEF DESCRIPTION OF THE FIGURES

FIG. 2A. Schematic diagram showing how dual lead electrodes allow each bipolar pair 3 to be twisted together for their entire length, sending signal directly to local differential amplifiers 4.

FIG. 2B. Schematic diagram showing how twisting of leads leaves only small loops at the head in which e.m.f. can be induced. Current induced in lead twists by motion and gradient switching will be self canceling.

FIG. 3. Diagram of an EEG data pathway. EEG signal is fed to a local differential amplifier 4, digitized and then sent out of the scanner room 7 via optical fiber for real time display and off-line analysis.

DETAILED DESCRIPTION

Figure 1A:
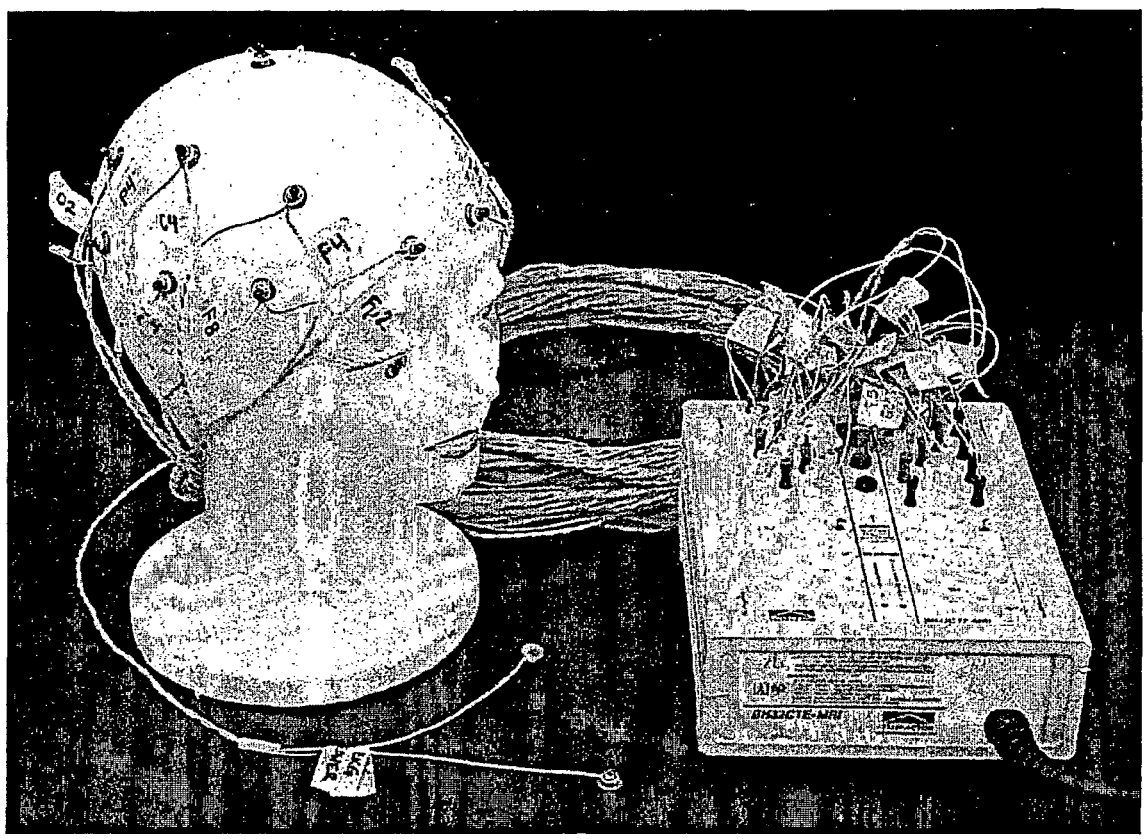
FIG. 1A. Digital photograph of chained bipolar dual-lead dress. Leads of consecutive electrodes are twisted together to reduce scanner artifact FIG. 1B. Schematic diagram showing electrode connectors 2 attached to the head of a subject 1 using standard electrode gel. Each of the connectors is attached to 2 electrical wires (typically constructed of carbon fiber material, which reduces magnetic artifacts). The wires from adjacent electrodes are twisted tightly together in pairs 3, where each of the two wires from a single electrode is twisted together with a different neighbor. The electrode pairs are then presented to the input of a differential amplifier 4 where the electrical potential difference is amplified to form the electroencephalogram. The inputs to the amplifiers are bridged such that the paired leads enclose a complete loop, thereby minimizing additional differential potentials between amplifiers. The wires are drawn in thick and thin lines for clarity only.

The invention is based on the discovery that contamination of a digitally encoded electrical signal can be reduced significantly by making use of a timing signal that is associated with the onset of a repeated contamination signal. Such a timing signal can be used to align the digitization of repeated contamination signals for determining an estimate of the contamination which can then be subtracted from the electrical signal. This method is particularly suited for use with electrophysiological signals, such as EEG, ECG, EMG and galvanic skin response (GSR), and for elimination of noise associated with concurrently used methods such as MRI. Although the examples described in detail herein address the application of the method to recording an EEG in the presence of fMRI, those skilled in the art of signal processing will appreciate that the method of noise reduction is applicable to recordings of other electrical signals, including, for example, audio recordings, wherein it is desired to reduce or eliminate one or more sources of repeated contamination.

Definitions

All scientific and technical terms used in this application have meanings commonly used in the art unless otherwise specified. As used in this application, the following words or phrases have the meanings specified As used herein, "electrical signals synchronized with respect to a timing signal" means that data corresponding to electrical signals recorded over a period of time are aligned so that a timing signal that occurs within each of the electrical signals recorded over time is superimposed by the alignment When an average is calculated of the electrical signals superimposed in this manner, the timing signal, as well as any other signal that recurs at a fixed time point relative to the timing signal, will be enhanced relative to non-recurring signals.

As used herein, "twisted" means united by winding, intertwining or coiling. A pair of electrical connections between a pair of electrodes and a differential amplifier is sufficiently twisted if the enclosed magnetic fields are substantially reduced.

As used herein, "a" or "an" means at least one, unless the context clearly indicates otherwise.

Methods

The invention provides a method of reducing contamination of electrical signals recorded in the presence of repeated interference contamination. The method comprises obtaining an electrical signal, wherein the electrical signal was recorded in the presence of a contaminating signal, and detecting a timing signal that occurs at a fixed time point during the electrical signal relative to the onset of the contaminating signal The method further comprises digitizing the electrical signal, wherein the digitizing begins with the timing signal. A plurality of digitized electrical signals is then analyzed, wherein the electrical signals are synchronized with respect to the timing signal, to obtain an estimated contaminating signal The estimated contaminating signal is subtracted from the digitized electrical signal, thereby reducing contamination of the electrical signal.

In a preferred embodiment, the analysis to obtain the estimate of the contaminating signal comprises averaging the electrical signals. In some embodiments, the analysis to obtain the estimate of the containing signal comprises calculating a weighted average of the electrical signals. The use of weighted averages can serve to achieve an adaptive artifact reduction. The estimate of the contaminating signal can be biased towards recent events, for example, by adding the nth electrical signal to a scalar multiple, w, of the prior estimate of the contaminating signal and dividing this by the sum of the series $1+w^2+w^3+w^4 \ldots + \ldots w^n$. The estimate of the contaminating signal can be multiplied by a scalar prior to the subtracting step.

Figure 19:
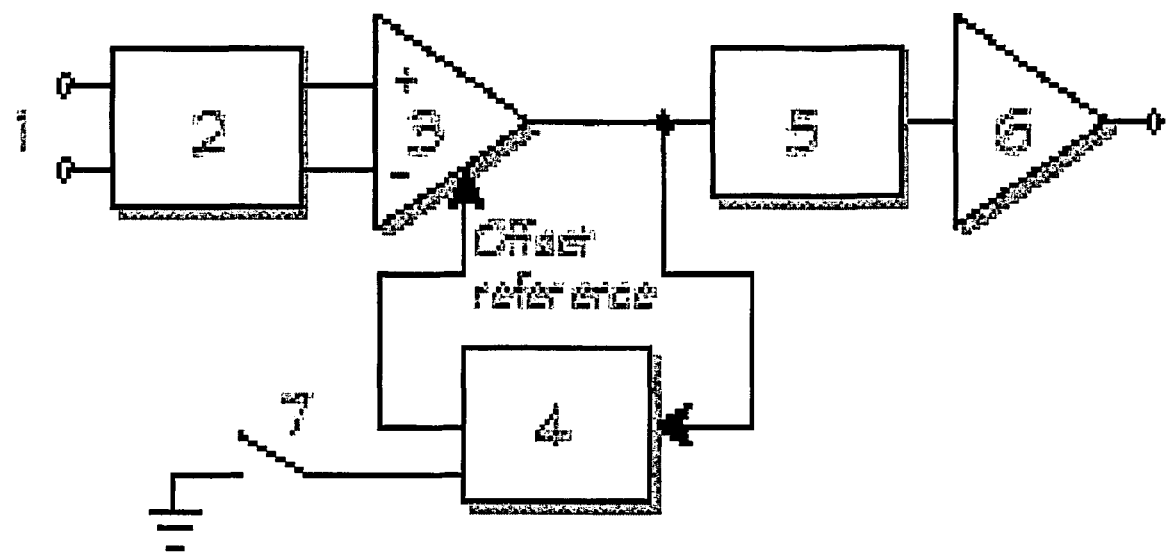
FIG. 19. Functional block diagram of MRI-compatible EEG amplifier.

FIG. 19 is a general functional block diagram of representative analog electronics useful in the method of the invention. The method performs optimally with an adequately linear electronic signal With reference to FIG. 19, signal is applied differentially at the input terminals 42. Using matched passive components for each lead 44, contaminating signal from sources such as radio frequency is attenuated before being differentially amplified using standard components 46. The differential amplifier 46 is commonly provided with an offset reference input, such that voltages appearing at this terminal are subtracted from the output Using a sample and hold device 52, the amplified DC offset potential, derived from the inputs, is first measured, then applied to the differential input amplifier 46. To attenuate sources of contamination that are above the highest frequencies of interest in the signal, an active low pass filter 48 is supplied. The filtered signal is buffered in the output amplifier 50 before being made available to the digitizer circuit. A switching means 54 is provided to the sample and hold circuit to allow detection of the input DC offset at any time desired.

Figure 14:
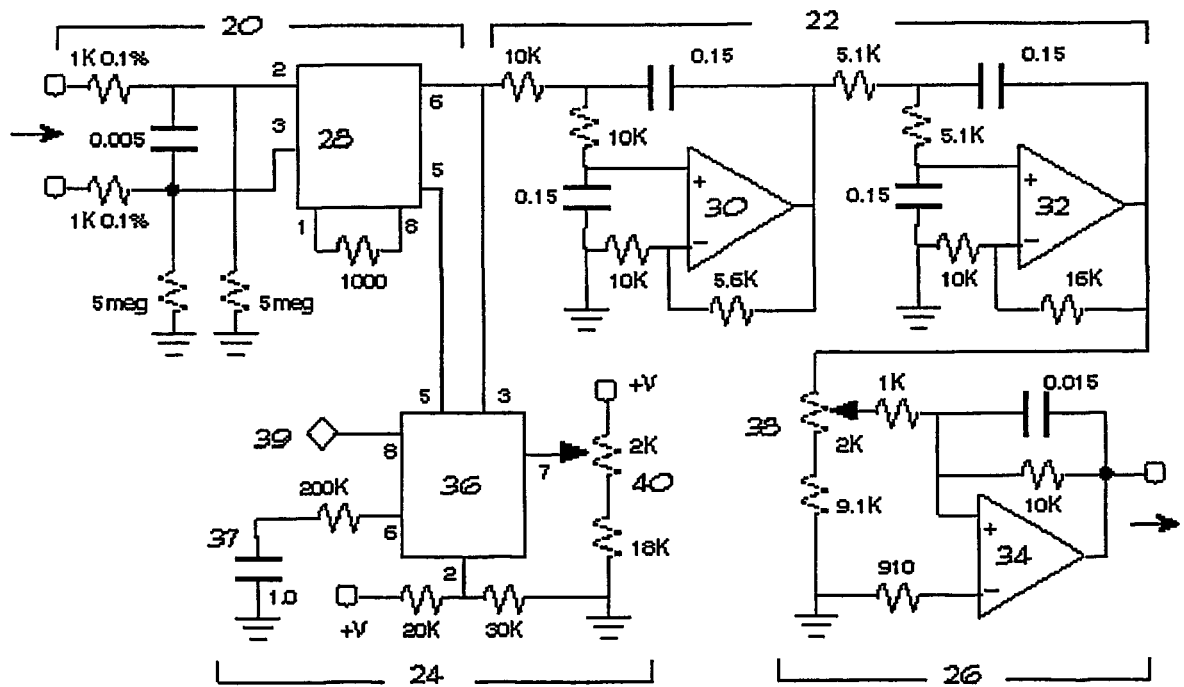
FIG. 14. Schematic representation of a low-cost offset nulling differential amplifier circuit for use in fMRI. Power supply connections are omitted for clarity. All capacitor values are in microfarads.

The circuit modeled in FIG. 19 is an example that is especially suited to the problem of recording electrophysiological signals during Magnetic Resonance Imaging. The functional logic of this diagram is shown m somewhat more detail in FIG. 20 which, in addition, illustrates a means of transmitting the EEG data out of the MRI suite. One skilled in the art will see immediately that many different circuit topologies are possible that will accomplish essentially the same function for this or other applications. For example, in some embodiments it may be desirable to apply a DC offset after the high pass filter (as indicated in the schematic of FIG. 14), or to avoid this step altogether, if significant DC offsets are not present in the signaL Further, in cases where there exists adequate headroom for the differential amplifier 46 to remain in its linear range for all expected inputs, it may be desirable to substitute a bandpass filter for 48. The passive filter 44 may be eliminated when any sis that reach the input to the input differential amplifier 46 are of suitably low amplitude to avoid saturation effects.

Figure 20:
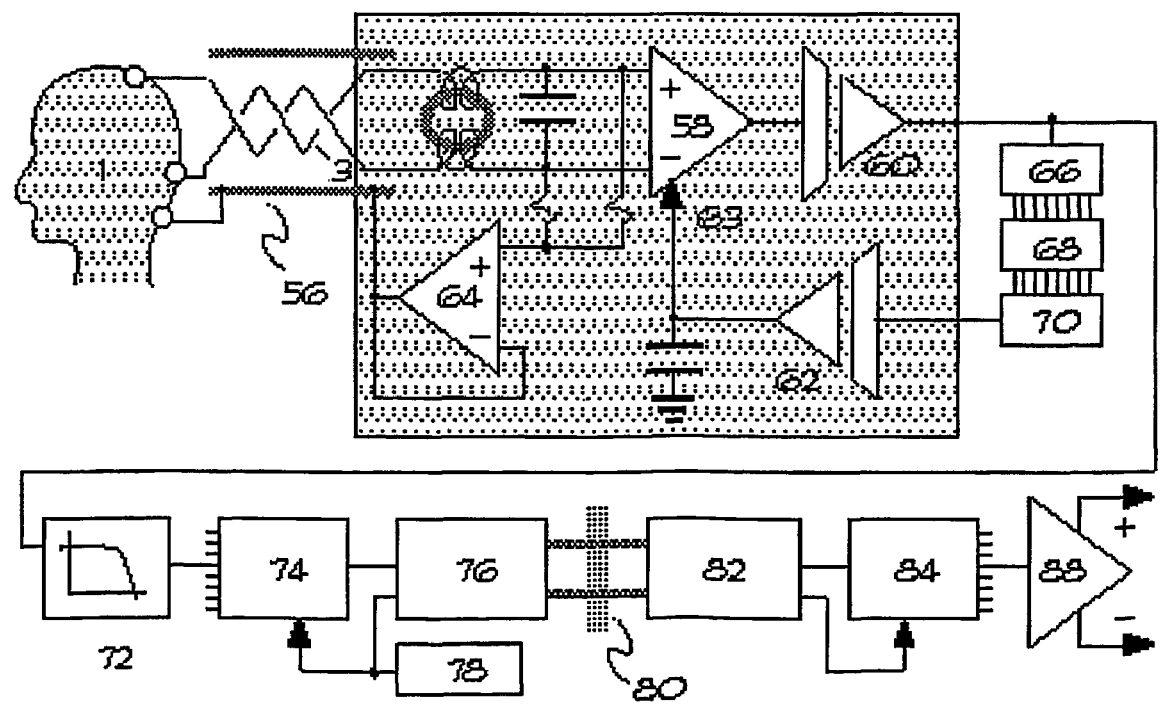
FIG. 20. Alternative differential amplifier circuit for use with fMRI.

With reference to the diagram shown in FIG. 20, EEG signal from the subject 1 is carried via twisted pair leads 3 to the input of a battery powered head amplifier. The inputs include RF attenuation via a series inductance and a parallel capacitor. These inputs are mixed in the inputs to shield driver 64, whose output is applied to a concentric shield 56 surrounding the twisted leads 3 and connected to the subject 1. The inputs are coupled to a differential amplifier 58, whose output is applied to an isolation amplifier, such as the ISO122 from Burr-Brown Corporation. This device, and a second similar device 62 provide electrical isolation to the subject and an added safety factor for EEG recording. The output from isolation amp 60 is sampled by an analog to digital convertor 66, whose digital output is stored in a latch 68 and converted to an analog voltage by digital to analog convertor 70. This output is applied as a DC correction 63 to differential amplifier 60 after electrical isolation by isolation amplifier 62.

The output from this head amplifier is presented to a low-pass filter to attenuate signal outside of the desired range of the EEG signal. This single channel output may be multiplexed with the outputs of other similar amplifiers by analog multiplexor 74 clocked by hardware timer 78. The output of the multiplexor 74 may be converted to an optical signal by optocoupler 76 and transmitted by,optical fiber, together with the dock signal to a second optocoupler 82 that is located outside of the MR shielded room through a penetration panel 80. De-multiplexor 82 is used to separate the signals from multiple amplifiers and its output may be presented to a differential line driver 88 for transmission of the signals over long distances to an analog to digital convertor for later processing.

Figure 21:
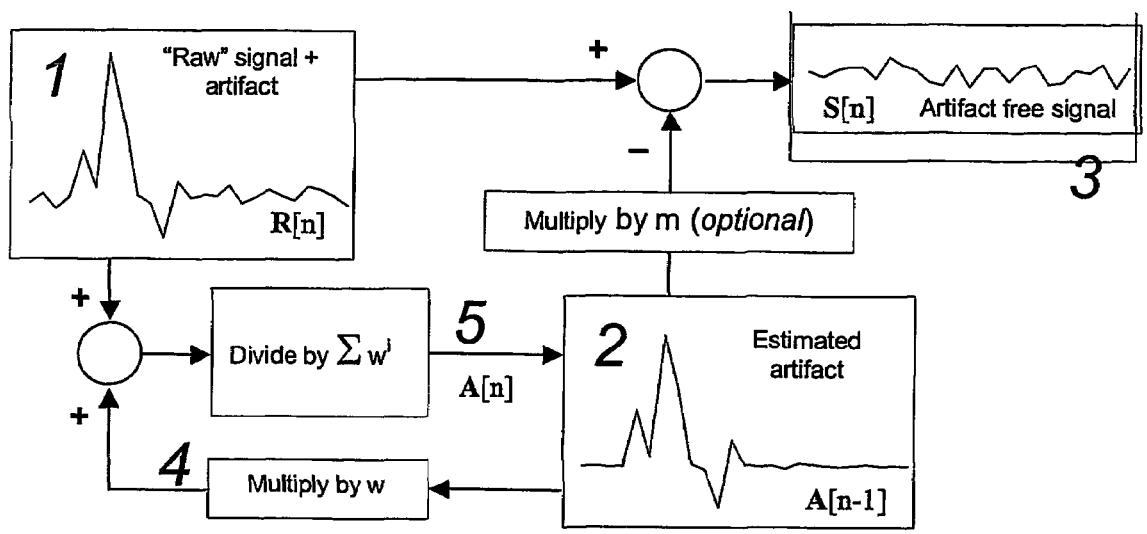
FIG. 21. Flow chart illustrating method of signal correction by artifact reduction.
Figure 22:
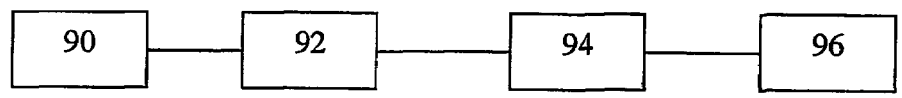
FIG. 22. Schematic illustration of elements of an apparatus of the invention.

FIG. 21 is a flow chart illustrating an application of the method of the invention. The raw digitized signal, containing both the desired signal and contaminating artifact are shown as (1) in FIG. 21. It is strongly preferred, for the invention to work optimally, that the signal in (1) be faithfully linearly) recorded and that the digitization be timed with adequate precision to the artifact To produce the corrected signal, an estimate of the artifact (2) is simply subtracted from the taw signal. Optionally, the estimate of the artifact may be multiplied by an amplitude constant, m, to account for differences in the magnitude of the coupling of the artifact to the signal recording system.

The artifact estimate can be computed as follows: Each time a new raw sample (1) is available, it is added to the current estimate of the artifact (2) which has been multiplied by a scalar amplitude constant, w (4). This summed signal is then divided by the sum of the series $1+w+w^2+w^3+\ldots$ resulting in a new representation of the artifact (5), which then replaces the value used for (2). When w is a number less than 1, the process results in a leaky average, where more recent signals have a greater influence on the estimated artifact (2) than do less recent signals. In this way, the system adapts to slow changes in the artifact, if necessary. For the purposes of this disclosure, we have called this implementation a "leaky averager."

More formally, if $R[n]$ is the $n^{th}$ raw signal collected, $A[n]$ is the estimated artifact for collection n, and $S[n]$ is the artifact-free signal:

$$A[n] = \frac{R[n] + wA[n-1]}{\sum_{i=0}^{n} w^i} = \frac{\sum_{i=0}^{n} w^i A[n-i]}{\sum_{i=0}^{n} w^i}, \text{ and}$$

$$S[n] \approx R[n] - A[n].$$

In the leaky averager discussed above, the influence of temporally distant data decreases with time. It would be possible to determine w adaptively by looking at the history of the estimated artifact If the artifact is changing quickly, w should be made smaller (reducing the influence of older frames on the current correction). Conversely, w should be large if the artifact is very stable. In the limit, if the artifact cannot change over time, $A[n]$ should be the simple average of all of the samples (w=1). If the algorithm is to be used in real-time, $A[n]$ will be the average of all samples until time n. If it is used "off-line" $A[n]$ will be the average of all samples both prior to and after time n.

It is possible to determine the value of m adaptively as well, approximating it as the amplitude that minimizes the correlation between $S[n]$ and $A[n-1]$.

The method is particularly suitable for electrical recordings which comprise an electrophysiological signal, such as an electroencephalographic recording, an electromyelographic recording, an electrocardiographic recording or a measure of galvanic skin resistance. The method is applicable as well to other types of electrical recordings, including audio recordings. In some embodiments, the interference comprises interference arising from inductively coupled magnetic fields. The interference can also comprise interference arising from other sources, such as alternating current (AC) line noise.

It is particularly advantageous that, in accordance with the invention, the digitizing can be performed at a sampling rate below the Nyquist rate for the contaminating signal In one embodiment, the electrical signal obtained is passed through a low pass filter prior to the digitizing, at a frequency of approximately one half of the frequency at which the electrical signal is sampled. For example, the low pass filter may pass signal frequencies of less than about 200 Hz.

The method can be performed concurrently with Magnetic Resonance Imaging of the subject In one embodiment, the electrical signal comprises an electrophysiological signal and the contaminating signal comprises gradient activity. Examples of a contaminating signal include radio frequency transmitter activity. In a preferred embodiment of the method, the digitizing is performed at a rate of about 200 to about 5000 samples per second. The digitizing can be performed at rates below 200 and above 5000 samples per second, with representative rates including 100, 250, 500, 1000, 2000, 3000, 4000 and 6000 samples per second.

The invention additionally provides a method of removing a DC offset from the electrical signal by analog subtraction prior to the digitizing. Preferably, the DC offset is measured and subtracted from the electrical signal using a difference amplifier. In one embodiment, the DC offset is measured by analog to digital conversion, and averaged over a time period long compared to the lowest frequencies of interest in the electrical signal. An example of such a long time period is approximately 10 times longer than the lowest frequencies of interest in the electrical signal For example, where lowest frequencies of interest are approximately 3 Hz, the time period is about 30 seconds. In one embodiment, the analog subtraction comprises converting the averaged signal to an analog voltage and electrically subtracting the averaged signal from the electrical signal through differential amplification. In another embodiment, the DC offset is measured in an analog integrator having a time constant long compared with lowest frequencies of interest in the signal.

The method of the invention is useful for electrophysiological recordings, such as an electroencephalogram that is recorded concurrently with magnetic resonance image acquisition. In a preferred embodiment, the electrophysiological recordings are used to inform interpretations of magnetic resonance images. The electrophysiological recordings can be used in a statistical analysis of change in intensity of the magnetic resonance signaL The method can further comprise determining a correlation between change in intensity of the magnetic resonance signal and a feature of the electrophysiological recording. The correlation can be used to make statistical images, or image maps, that represent an association between the electrical signals and the intensity of the magnetic resonance signal intensity. In one embodiment, the feature of the electrophysiological recording comprises a time course of signal intensity change in defined frequency bands contained in the electrophysiological recording.

The defined frequency bands can be selected to correspond to standard ranges used for clinical interpretations of the electroencephalogram. Representative standard ranges are selected from the group consisting of from 0 to approximately 4 Hz (the Delta band), from approximately 4 to approximately 8 Hz (the Theta band), from approximately 8 to approximately 12 Hz (the Alpha band), from approximately 12 to approximately 30 Hz (the Beta band), and from approximately 30 Hz and greater (the Gamma band). Typically, the frequency bands for this application will not extend beyond 300 Hz. In one embodiment, the method further comprises convolving the time course of the electrophysiological signal with an estimate of the magnetic resonance hemodynamnic impulse response function. In this embodiment, the time course of the electrophysiological signal is suitably conditioned to more accurately reflect the anticipated time course of the magnetic resonance signal change.

The invention additionally provides a method of reducing magnetic interference during electrophysiological recording from a subject by measuring an electrical potential difference between a pair of electrodes, wherein the pair of electrodes communicate with a differential amplifier via electrical connections, the method comprising twisting the electrical connections together, thereby reducing magnetic interference. Also provided is a method of reducing magnetic interference during electrophysiological recording from a subject by measuring an electrical potential difference between a pair of adjacent electrodes, wherein each electrode comprises two leads, the method comprising twisting each lead together with a lead of an adjacent electrode, thereby reducing magnetic interference. In one embodiment, the electrophysiological recording comprises an electroencephalographic recording. The method can be performed concurrently with Magnetic Resonance Imaging of the subject Apparatus The invention further provides an apparatus for processing digitized electrical signals in the presence of a repeated contaminating signaL The apparatus comprises a signal processor 90 adapted to receive a recording of an electrical signal; a detector 92 adapted to detect a timing signal that occurs at a fixed time point during an electrical signal relative to the onset of a contaminating signal; a signal accumulator 94 to contain the estimated contaminating signal; and a processor 96 adapted to subtract averaged waveforms from an electrical signal. Representative variations of the apparatus are described in FIGS. 3, 14, 19, and 20.

The signal processor 90 adapted to receive a recording of an electrical signal may be, for example, an electronic circuit (IC) consisting of a integrated differential amplifier such as a an INA114 from Burr Brown Corp., with a DC offset reference provided through measurement by a sample and hold IC such as the LF298 from National Semiconductor corporation, a low pass active filter and an output buffer all made using standard operational amplifier ICs. In this embodiment, the detector can also include a means of analog to digital conversion, such as a National Instruments NI 6031E installed in a personal computer.

The detector 92 adapted to detect a timing signal that occurs at a fixed time point during an electrical signal relative to the onset of a contaminating signal may be, for example, an optoisolator IC whose output is conditioned using an IC such an LN555 from National Semiconductor corporation to produces a TM compatible trigger signal which is then presented to an analog to digital convertor such as a National Instruments NI 6031E installed in a personal computer.

The signal accumulator 94 may be implemented, for example, in software in the 'C' programming language as a vector of numbers, or in the National Instruments Lab View programming language as an array of numbers. Either of these may be executed on a personal computer. The signal accumulator 94 can be, for example, a signal averager. Other methods, in addition to signal averaging, can be used to generate an estimate of the contaminating signal.

The processor 96 adapted to subtract averaged waveforms from an electrical signal may be implemented, for example, as a processing routine in the 'C' programming language or the National Instruments Lab View programming language running on a personal computer. Those skilled in the art will appreciate variations on the above examples of apparatus elements that will serve the same processing, detecting and accumulating functions in accordance with the methods of the invention.

Overview of EEG and fMRI in Simultaneous Recording and Mapping

Electroencephalography (EEG) is established firmly as a means to probe changes in electrical signals recorded from the scalp that accompany behavioral tasks, and as a market for clinical, cognitive or neural states. Determination of the three-dimensional localization of the EEG signal is ambiguous because the relationship between the actual position of multiple electrical dipoles and the distribution of electrical potentials detected at the scalp has no unique solution. Functional Magnetic Resonance Imaging (fMRI) uses modulations in the magnetic resonance signal that depend on variations in blood oxygenation to distinguish brain regions whose activity is increased or decreased with task demands. The following describes a set of solutions to the technical problems in simultaneous recording of fMRI and EEG and shows that data from the two methods may be combined to create tomographic images indicating brain regions whose activity changes as a function of EEG signal intensity in the classically defined spectral bands.

Significance and Interpretation of the EEG

Study of the electroencephalogram (EEG) is more than a century old (Caton 1875). The phenomenon is highly robust namely that electrical potentials exist at the surface of the head that are correlated strongly with ongoing cerebral activity and fluctuate with sleep stages (Rechtschaffen and Kales 1968; Buchsbaum, Mendelson et al. 1982; Benca, Obermeyer et al. 1992), emotional state (Davidson, Schaffer et al. 1985; Davidson 1988; Ekman, Davidson et al. 1990; Lambert and Robertson 1999), attention (Klimesch, Doppelmayr et al. 1998; Wrobel 2000), therapeutic drug doses (Loo, Teale et al. 1999; Alvarez, Lombardi et al. 2000), traits, such as "aggressiveness" (Fishbein, Herning et al. 1989) and with circulating levels of a wide variety of drugs of abuse (Cezayirli, Little et al 1975; Maykut 1985; Tokunaga, Takeichi et al. 1989; Abraham and Duffy 1991; Mannelli, Janiri et al. 1993; Bauer, Gross et al. 1997). Despite the considerable history and attention to this measurable phenomenon, the origin of the EEG signal and the localization of its sources (presumably cerebral), is still not known. The situation is somewhat more favorable with evoked potentials (EP's, in some contexts known as evoked response potentials or ERP's) for which the temporally discrete nature, and the motion across the scalp, of the surface potentials combine to give a better indication of the deep dipole or dipoles that generate the signals, but it has been difficult to test directly the relationships between scalp EP and brain activity, especially for sources significantly below the cortical surface. For example, attempts to localize the generators of the brainstem auditory evoked response by simultaneous recording with depth electrodes or correlation with lesions have been conclusive for only a subset of the waveform components present in the signal (Starr and Achor 1978; Chiappa, Gladstone et al. 1979; Achor and Starr 1980b; Achor and Starr 1980a; Goldie, Chiappa et al. 1981; Cohen and Britt 1982; Chiappa and Young 1985).

When Caton first reported on the resting and task evoked electrical activity of the brain in animals (Caton 1875), he was able to determine that there was a transcortical electrical potential that changed during periods of functional activity (sensory stimulation). Caton noted that, "*Feeble currents of varying direction . . .*" were generally present between different points on the cortical surface. Some years later, Berger noted that scalp potentials could be recorded in humans with properties similar to those of Caton's cortical potentials (Berger 1929) and he soon realized that this electroencephalogram varied according to the mental state of the subject (Berger 1930). By 1930 Berger had described what he called the alpha rhythm, being relatively high amplitude oscillations in the range between 8 and 12 Hz that were associated with drowsiness. It is now accepted that alpha activity is associated with a relaxed, awake state, usually with eyes closed.

EEG is now a routine and essential test in clinical neurology. It provides diagnostic information that cannot be gathered through any other commonly obtainable means. Indeed, its indispensability derives from this lack of other routine clinical tools to assess a broad region of cerebral neurophysiology with high temporal resolution. EEG depicts moment-to-moment changes in cerebral cortical function, and thus is valuable in any clinical context where such information would guide medical decision making. Such situations are not limited to electrophysiologic abnormalities, as other pathologic processes often affect neuronal function and, thus, impact the EEG. These include ischemia, metabolic alterations, mass effect, and infection among others (Markand 1984).

Because it represents abnormality in neuronal electrophysiology, epilepsy is a common clinical problem that warrants the use of EEG (Engel 1984). Despite a central place in clinical neurology that has endured over most of the past century, the basis of EEG is still understood poorly. The generators of the potentials that sum to create the waves are understood better (McNamara 1994). However, the interaction between cell populations to create electric fields at the scalp has proven difficult to study.

By performing fMRI during EEG, one may obtain complementary information and greater understanding of EEG and the clinical conditions that EEGs may indicate. It appears that solid results that characterize the relationship between scalp potentials and local brain activity will offer great value in guiding the clinician to isolating specific abnormalities. In fact, there are already scattered reports that interictal spike discharges, associated strongly with clinical epilepsy, might be used in combination with functional MRI (Warach, Ives et al. 1996; Seeck, Lazeyras et al. 1998; Krakow, Woermann et al. 1999; Patel, Blum et al. 1999; Symms, Allen et al. 1999; Schomer, Bonmassar et al. 2000) (or PET (Henry, Sutherling et al. 1991)) to identify surgically resectable lesions, and tomographic localization via MEG has been suggested as a means to guide such resections (Stefan, Schneider et al. 1990). The use of fMRI during epileptic seizures has also been tested with success by Jackson (Jackson, Connelly et al. 1994).

EEG and Imaging in Sleep Disorders and Staging

Based on unit activity, stimulation studies, and lesion studies in non-human mammals, brain regions active in non-REM sleep include the anterior hypothalamus, dorsal bulbar reticular formation, and nucleus of the solitary tract (Jones 2000). Regions likely associated with REM activity, and possibly the generation of wakefulness, include the posterior hypothalamus, ventral mesencephalic pons, basal forebrain, and pontine reticular formation. Such localized brain activity should also be visible in humans through functional neuroimaging. Both PET and SPECT have been used to examine regional activity changes (via cerebral metabolism and blood flow respectively) with sleep stage (determined electroencephalographically). These imaging studies have broadly indicated that areas thought to be involved in the active generation of rapid eye movement (REM) sleep are active during this stage of sleep and in non-rapid eye movement (NREM) sleep.

Maquet and colleagues Naquet, Dive et al. 1990) noted that rates of cerebral glucose metabolism (rCMRGlc) during NREM are lower, overall, compared to those during wakefulness (most notably in the thalamic nuclei), and that REM sleep rCMRGlc is comparable to the awake state. Furthermore, the greater the depth of the NREM sleep (i.e., the greater the amount of cortical synchrony), the lower the rCMRGlc (Ingvar, Baldy-Moulinier et al. 1965; Madsen, Holm et al. 1991; Maquet, Dive et al. 1992). Especially intriguing is the observation that changes in cerebral blood flow show substantial regional heterogeneity. REM-associated increases in rCBF have been observed in the pontine tegmentum, thalamus, limbic areas, cortical areas (notably the anterior cingulate cortex), and visual association areas, with a decrease in the dorsolateral prefrontal cortex, parietal cortex, posterior cingulate cortex, and precuneus (Madsen, Holm et al. 1991; Madsen, Schmidt et al. 1991; Maquet, Peters et al. 1996; Nofzinger, Mintun et al. 1997; Braun, Balks et al. 1998). Interestingly, rCBF increases have been observed in the extrastriate visual areas, though not the primary visual cortex which may, as has been hypothesized by those authors, be indicative of some sort of visual memory activation during sleep (Braun, Balkin et al 1998; Maquet and Phillips 1998; Maquet 1999).

As an example of the relevance of imaging during sleep, current studies suggest a role for sleep in memory consolidation, based on changes in sleep blood flow as a function of daytime activities (Maquet, Laureys et al. 2000). There are also important correlations between sleep and a variety of psychiatric disorders (Benca, Obermeyer et al. 1992) that might expose sleep physiology as a marker for these problems. But, due to the coarse temporal resolution of PET and SPECT Nofzinger, Mintun et al. 1998) and the relatively rapid changes in brain activity during sleep, neither of these imaging methods is suited ideally for this purpose. Very recently, there have been reports of the use of fMRI in assessment of localized signal changes that take place dung sleep (Lovblad, Thomas et al. 1999; Horne 2000) that indicate an increase in occipital lobe activity and a decrease in the frontal lobes during REM, in agreement with the PET findings. However, such studies cannot be considered definitive without the incorporation of sleep staging by electroencephalographic means (Lovblad, Thomas et al. 1999). EEG-fMRI provides an excellent solution.

The sleep electroencephalogram can be defined by characteristic frequency patterns, and brief electrophysiological phenomena such as k-complexes and sleep spindles. Furthermore, during REM sleep, there is a descending suppression of muscle tone, saccadic eye movements, and the loss of the cortical synchrony that is a hallmark of NREM sleep. Only with temporal resolving power of fMRI will it be possible to study activations associated with these transient events. One application of the invention is to assess changes in regional brain activity using fMRI and to correlate such activity to classically defined sleep architecture and features. For example, the invention can be used to seek an understanding the brain activity that underlies the general lack of responsiveness to external stimuli, the apparent gating of motor output and dream states.

Functional MRI (fMRI) is now an established method for the localization of focal areas of brain activity, chiefly in humans (Cohen and Bookheimer 1994). Although it is assumed that the fMRI signal arises from local changes in blood oxygen content (Ogawa, Lee et al. 1990a; Ogawa, Lee et al. 1990b; Kwong, Belliveau et al. 1992; Ogawa, Tank et al. 1992), this theory has not been subjected to extensive direct testing, and the mechanism of coupling between neuroelectrical activity and MRI signal changes is still the subject of speculation. Nevertheless, the observed areas of signal increase correlate well with both extensive literature on neurophysiology and, more recently, with electro-corticography derived of humans in surgical settings (Schulder, Maldjian et al. 1998; Roux, Boulanouar et al. 1999; Lurito, Lowe et al. 2000). While there is a growing literature that attempts to use the localization power of fMRI to aid in the interpretation of the study of evoked responses, there is a striking paucity of reports that attempt to reconcile the findings in EEG with functional MRI.

The classical or posterior alpha rhythm is found mostly in occipital, parietal, and posterior temporal regions (Adrian and Matthews 1934), and first emerges at about 4 months of age as a 4 Hz oscillation, present with eyes closed and blocked with eyes open. The frequency of this rhythm increases with age, reaching about 8 Hz by age 3, and by about age 10, it reaches the average adult frequency of 10 Hz (Petersen and Eeg-Olofsson 1971). Although recognized since the beginnings of EEG, little is known about the functional significance of this alpha rhythm; it reflects essentially a state of relaxed wakefulness, and can be used as an indirect measure of brain activation, for increased alpha band activity is thought to correspond to decreased activity in underlying cortex (Shagass 1972). Thus, decreased alpha activity, or stimulus-induced alpha blocking, has been termed "event related EEG desynchronization" (Pfurtscheller and Aranibar 1977). Davidson and colleagues have shown that alpha asymmetry recorded in anterior regions correlates with emotional reactivity, and that these asymmetries appear trait-like in waking and in sleep (Petersen and Eeg-Olofsson 1971). Studies in animals have suggested the thalamus as a possible generator of the alpha rhythm (Petersen and Eeg-Olofsson 1971). Lopes da Silva demonstrated significant thalamocortical coherences in dogs between lateral geniculate nucleus and pulvinar and the cortex (Lopes da Silva, Lierop et al. 1973; Lopes da Silva, Vos et al. 1980). Recently, in humans, Lindgren and colleagues showed an inverse correlation between EEG alpha power and thalamic metabolic rate in normal subjects using PET (Lindgren, Larson et al. 1999).

Challenges in Combining fMRI and EEG

Even in the best of circumstances, EEG signals recorded in the clinical environment are relatively noisy. The effective input resistances are large, and the signals are small. As a result, Boltzmann noise limits the ultimate signal to noise ratio. With a typical 5 MΩ input impedance, the Boltzmann noise will be approximately 1.5 μV ($v_{rms}=\sqrt{4kTBR}$, where k is Boltzmann's constant, T is the temperature, B is the bandwidth and R is the equivalent resistance) even over the limited bandwidth of 100 Hz or so used in the EEG. Since the scalp potentials are typically only a few μV, the signal to noise ratio (SNR) of the EEG seldom exceeds 100:1. Because EEG is often analyzed in the spectral domain over narrow bandwidths, the effective SNR for detection of band-limited signal (for example, alpha intensity) may be somewhat higher.

Beyond the thermal noise limit, other factors further reduce the SNR of EEG. Cardio-electric (EKG) and myo-electric (EMG) signals add contamination. Corruption by the EKG is variable across individuals; though always present, it is usually smaller than the EEG, but at times can become comparable in amplitude. The EMG is typically a contaminant for only brief periods of head or facial muscle contraction, such as eye blink, grimace, etc. The methods of the invention actually serve to reduce the EKG artifact that would be present whether or not the subject is scanned in the magnet All told, these sources of noise reduce the useable dynamic range of the total EEG signal dramatically for virtually all purposes.

Noise in the MRI Environment

The noise environment for EEG becomes radically worse when subjects are placed inside an MR imaging system. Almost all of the noise sources, however, are coupled magnetically to the EEG. Several of these are non-biological, including: amplifier noise in the shim and field gradient amplifiers; large time-varying magnetic fields induced by the field gradients during scanning, and radio-frequency signals generated by the scanner for magnetic resonance induction. By Faraday's law, the magnitude of the voltage induced by these time varying fields is proportional to the first time derivative of the flux, and thus to the amplitude of the magnetic field, its first time derivative, and the area enclosed by any conducting loop. More specifically:

$$e.m.f.=d\phi/dt,$$

where e.m.f. is the induced electromotive force, and Φ is the magnetic flux. In MR imagers these sources cannot be reduced in any practical way. The MR imaging gradients in state-of-the-art imaging instruments slew at an extremely high rate; the field gradients on a typical scanner operate at 80 T/sec and are thus major sources of noise; the newest generation of MR instruments, with local head gradients, will slew two to three times faster. The RF pulses, though only about 50 milliGauss, have fundamental frequencies, at the 3 Tesla operating field, of 128 MHz. Slewing at 4000 T/s, they too are large sources of noise.

Physiological noise sources are present also. Even small motions of the subject are coupled to the EEG as the leads move within the large static magnetic field. Not only minor fidgeting, but also the motion of the whole body with each heartbeat (the ballistocardiogram), produces signal in the μV to mV range.

DC Offsets and Transient Recovery

The scalp electrical potentials used in the EEG contain both time varying and static (DC) components. Often the DC signal is much larger than the EEG, but it is seldom of interest for clinical diagnostic purposes (note reference to true DC offsets, not to slowly varying potentials), as it contains essentially no information. However, it does cause trouble for the EEG in several ways. Typically, the DC offset increases the dynamic range needed to digitize the EEG signal For example, the EEG signal may be only a few μV, while potentials of a few mV may exist between electrodes, or as a result of the chemical electrode potential. The signal digitization depth will be reduced by the ratio of the EEG to the DC potential. For example, assuming a DC offset of 10 mV and an EEG signal of 10 μV, the 4096 different levels representable by a 12 bit analog to digital converter (ADC) will be reduced to only 4 levels for the EEG. Clearly this loss is unacceptable, as quantization noise will dominate the signal.

For these reasons, conventional EEG amplifiers are equipped with AC-coupled (high pass) inputs, usually a capacitor separating the first stage amplifiers from the input to the ADC. The inputs will usually have time constants of several seconds, allowing frequencies of 1 Hz or so to pass unattenuated. One consequence of this AC coupling is that it creates a time constant for signal recovery if the input saturates. Because these filters must pass very low frequencies, the recovery time for the analog signal to come back to the center of its nominal range can be quite long.

In fMRI, the recovery time associated with AC coupling is a substantial problem, as the gradient-induced artifacts (tens of mV) can be large enough to saturate the input stages, pinning them to the positive or negative supply rails for several msec. When the gradients cease, the settling time of the high pass filter greatly outlasts the gradient event A recent paper studying EEG-fMRI combinations, reported that, "The EEG could not be interpreted during the artifact caused by the excitation pulse, but the recording becomes readable in less than 1 second (approximately 100 msec) after completion of the BURST" (Hennig and Hodapp 1993; Lovblad, Thomas et al. 1999). This problem can be mitigated by using the methods of the invention, including an artifact-reducing electrode configuration and an input amplifier (Grass-Telefactor) with enough headroom to stay out of saturation prior to the high pass stage. As disclosed herein, the invention further provides a mote complete solution that avoids the high pass filter completely.

Gradient Noise

The magnetically-induced gradient noise is of very large amplitude (milliVolts in a typical scanner) as compared to the EEG, especially in the context of echo-planar imaging. One group has implemented a correction scheme for gradient artifacts that is similar to a scheme that group developed for ballistocardiogram removal (Allen, Josephs et al. 2000). Because the fundamental frequencies of the gradient activity are much higher, they developed special recording hardware that allowed them to use a much higher digital sampling rate of 5 kHz, which they selected as being rapid compared to the nominal Nyquist frequency for the gradient waveshapes. Unfortunately this is not sufficient, as sampling at the Nyquist rate guarantees only against aliasing of the higher frequencies into the pass band, but does not effectively remove the artifact.

Figure 9:
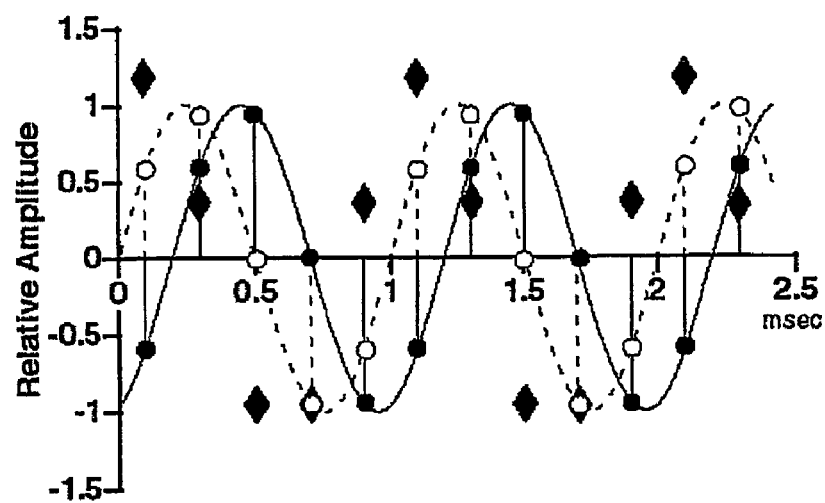

For example, assume that there is an undesired signal consisting of a sinusoid at 1000 Hz contaminating the EEG, which is sampled digitally at 5 kHz. Because the gradient and digitization activity are clocked independently, and are asynchronous, the phase at which the artifact is sampled can vary by as much as $2\pi/5$ (72° or 200 µs at this frequency). Over extended sampling periods (typically five minutes or more in an imaging experiment), it is likely that the relative timing of the scanner and sampling clocks will differ to this degree. FIG. 9 shows this effect In this simulation, the artifact is assumed to have been sampled at the points indicated by closed circles. At a later time, the sampling has drifted with respect to the gradients by 200 µs (dashed line, open circles). The difference signal is the residual artifact, in this case just over 17% greater than the uncorrected signal. To mitigate this problem, the Allen group has adopted a sophisticated interpolation scheme that is successful in minimizing the residual contamination. The present invention provides a much more effective approach based on an alternative formulation of the digital sampling problem.

The methods disclosed herein have made it possible to effectively eliminate contamination of the ERG signal by the most severe sources of noise present during MRI scanning in general, and in functional MRI in particular. In one embodiment described herein, the method has been used in the construction of tomographic maps of brain activity corresponding to the energies in spectrally-defined components of the EEG.

Theory

Digitization

Figure 10:
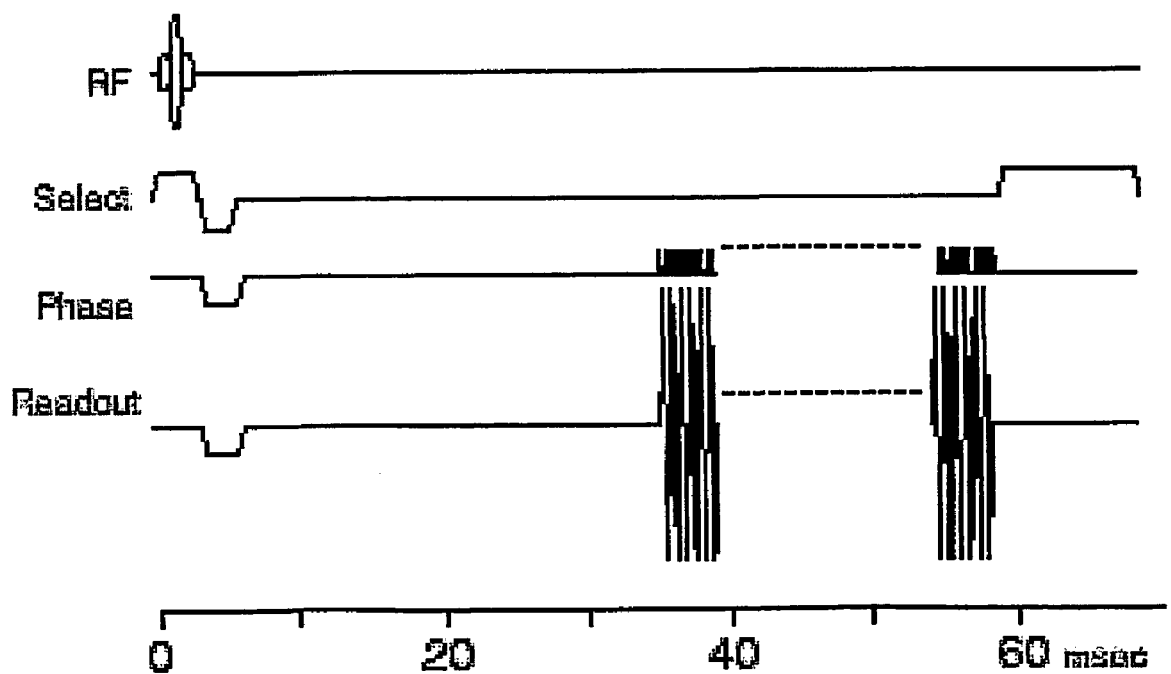
FIG. 10. Depiction of timing for the gradient echo EPI pulse sequence used in FIGS. 11-13.

The artifact from gradient activity is large and contains substantial energy at high frequencies. FIG. 10 shows the timing of a typical echo-planar imaging sequence, as used in typical functional studies. The lines for Select, Phase and Readout indicate the amplitudes of the three orthogonal magnetic field gradients used for imaging. The fourth line indicates the timing of the radio frequency channel (only the amplitude envelope is shown for the RF, as the carrier frequency of 128 MHz is not visible at this resolution.) Immediately apparent is the very large high frequency (1400 Hz) oscillation of the readout-gradient (shown at half the vertical magnification of the other gradients).

Figure 11:
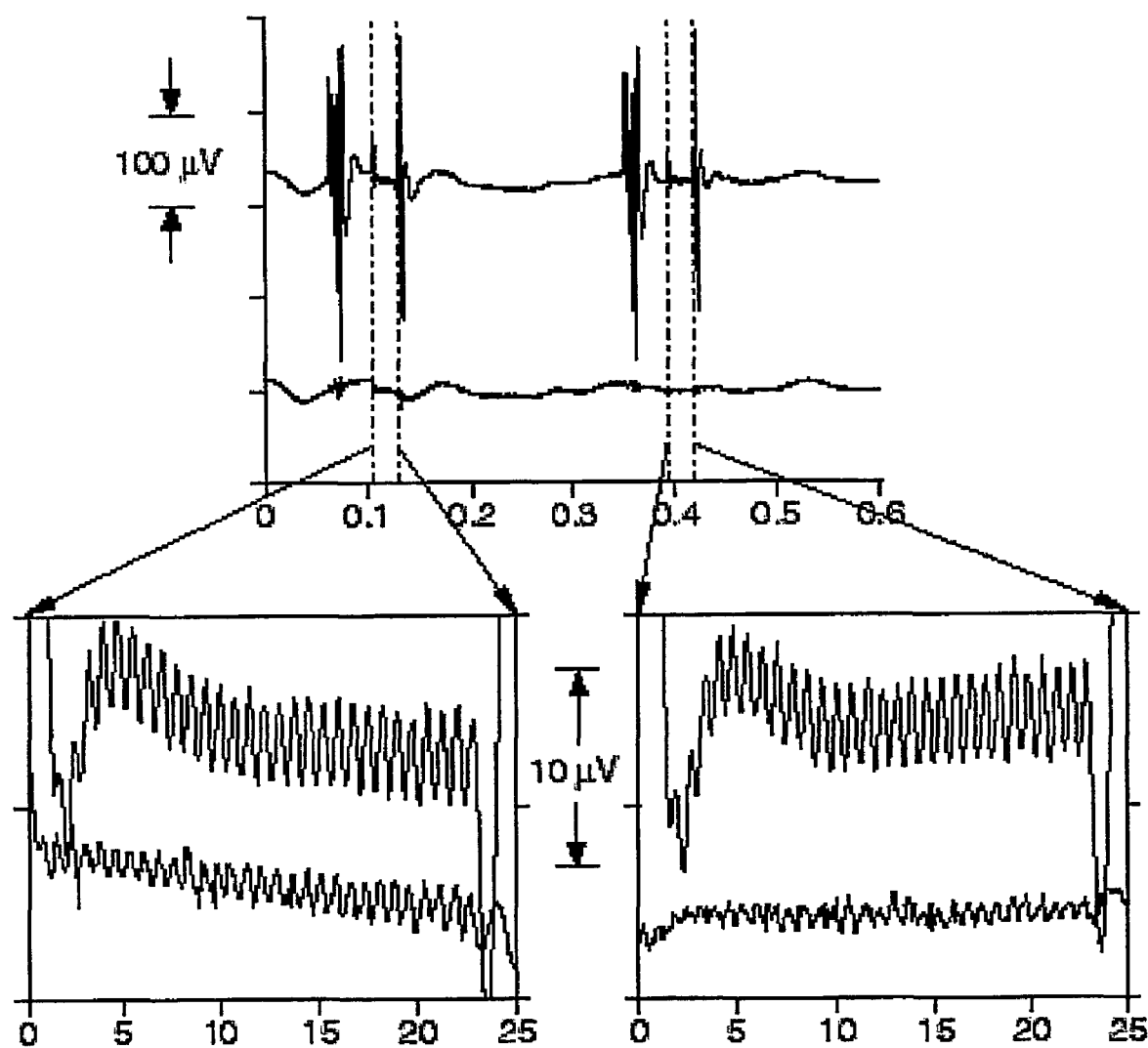
FIG. 11. Top: Graph representing uncorrected and corrected signals obtained during imaging, using 10 kHz sampling. Bottom. Enlarged (10×) views of the 25 msec periods indicated in dashed lines (uncorrected signal in dotted lines). Note that the artifact suppression varies from cycle to cycle, as a result of phase errors.

FIG. 11 shows raw signal recorded from an EEG system at a sampling rate of 10 kHz, following analog low-pass filtering at 100 Hz. The insets on the bottom of this figure show expanded representations (10×) of the indicated regions of the signals. When EEG data are acquired during scans, the MRI field gradients induce voltages much higher than the cortical signal. Comparing this and the previous figure reveals that the magnitude of the high frequency components is reduced dramatically by the low pass filter, and that the residual artifacts outlast the gradients themselves.

Though the low pass filter provides at least 100-fold reduction in the 1400 Hz oscillations, it does not remove the transients as these gradients turn on and off. These contain energy at very low frequencies, as well. The AC coupled input stage, in this traditional amplifier, is responsible for the extended ring-down of the artifacts (the saturation recovery alluded to previously), although it is much better than the 0.1 to 1 s ring down reported by others (Lovblad, Thomas et a. 1999), presumably due in large part to the attenuation provided by the differential recording apparatus, which helps to prevent the amplifiers from going into saturation.

When applying cyclic averaging techniques to this data set (Allen, Josephs et al. 2000) as shown in FIG. 11, they are reasonably effective in attenuating the effects of the low frequency components, they are largely ineffective at removing the high frequency content This, as described above, results from the asynchronous sampling. The residual (worst case) error from sampling too slowly can be predicted from the maximum phase shift, $\phi$ $$\varepsilon = \cos(2\pi ft + \varphi) - \cos(2\pi ft)$$
$$= \cos(2\pi ft)(\cos\varphi - 1) - \sin(2\pi ft)\sin\varphi$$

The maximum phase shift, $\phi$, that can occur at a given sampling rate is equal to $2\pi f_0/f_s$, where $f_s$ is the sampling frequency, and $f_0$ is the frequency of the EPI readout Comparing the residual artifact during the two scan periods (two expanded frames at bottom of FIG. 11) reveals that the cancellation efficiency is unstable as a consequence of the asynchronous timing of the gradient activity and sampling device, which causes the sampling offset, $\phi$, to drift over time.

As the sampling rate is increased, the cancellation will become more accurate. Using the approximation that for small $\alpha$, $\sin \alpha \approx \alpha$ and $\cos \alpha \approx 1$, one can see that in this regime $\epsilon$ is approximately proportional to $\phi$. It follows that if the artifact must be suppressed by 100 fold, the signal must be digitized at approximately $100*2*\pi$ times the highest frequency. of interest, in this case (the 1400 Hz readout) about 880 kHz/channel, which is impractical for reasons of both cost and overall data handling. In any case the acceptable sampling error is predicted readily by this formula given the low pass filter characteristics and the desired final signal to noise.

Figure 12:
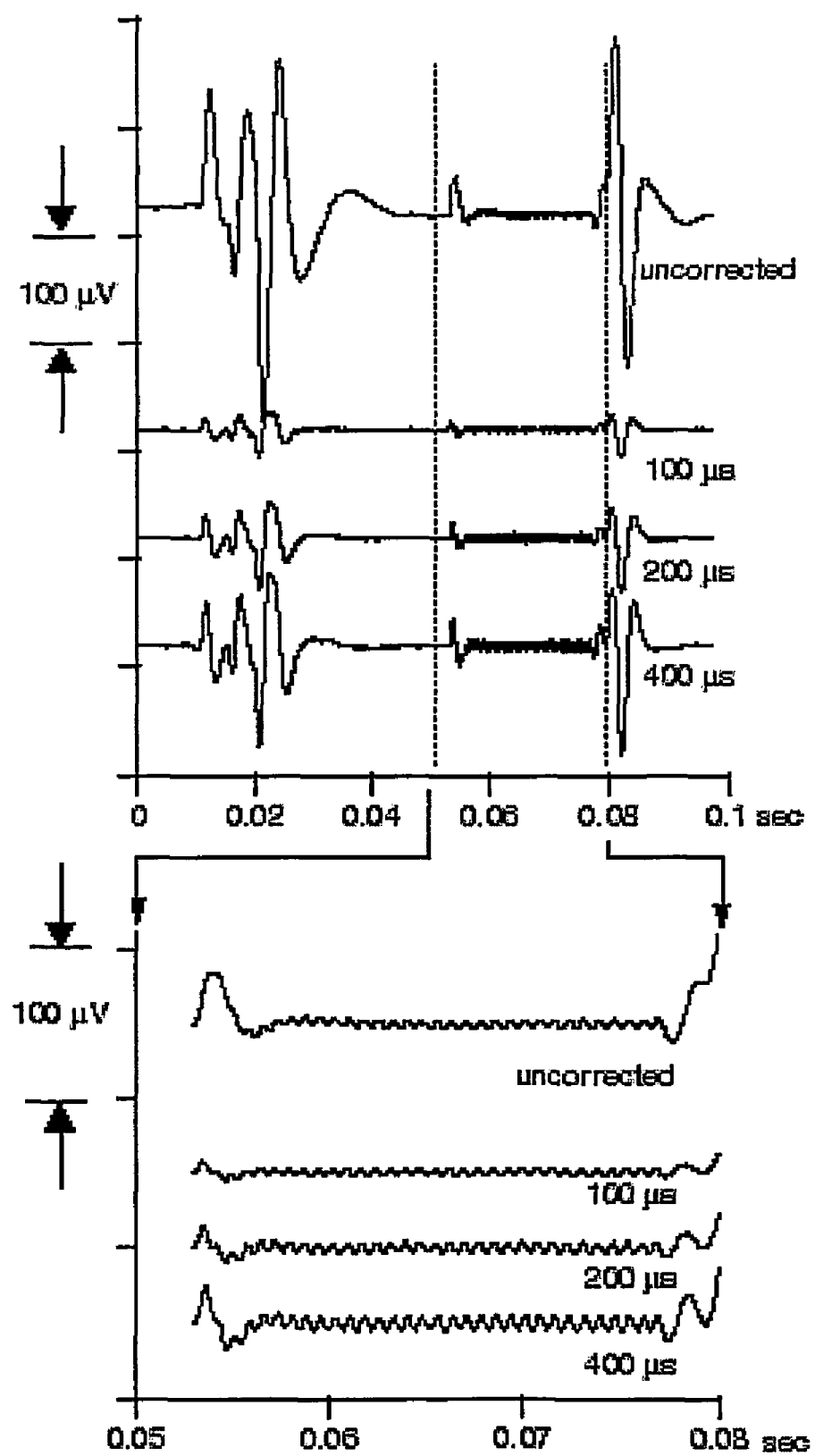
FIG. 12. Graph showing simulation of the effects of sampling rate on the efficiency of gradient artifact suppression. The trace at the top is actual EEG data recorded at 10 kHz during an echo-planar imaging sequence. The three traces below it are the difference between the original signal and a sample lagged at 100 μs, 200 μs and 400 μs as indicated (the worst case errors for 10 kHz, 5 kHz and 2500 Hz sampling). The graph below shows a detail of the period during which echo-planar readout occurs.

The data above were sampled at 10 kHz, well above the 2800 Hz Nyquist criterion for the high frequency components of the signal. FIG. 12 shows the efficiency of artifact subtraction based simply on rapid sampling. On the top is shown the raw artifact. Below it is shown the residual artifact that remains after subtraction if the tiring of the sampling and the scanner have drifted from synchrony by 100, 200 and 400 μsec, corresponding to the worst case errors for sampling at 10 kHz, 5 kHz and the approximate Nyquist rate of 2500 Hz, respectively. It is immediately apparent that the residual act, after subtraction, is large even with the smallest timing offset In the graph at the bottom of FIG. 12, which shows in greater detail only the echo-planar readout segment of that data, one can see that the simple subtraction actually increases the magnitude of the artifact, as predicted in the equation above (and in FIG. 9).

Figure 13:
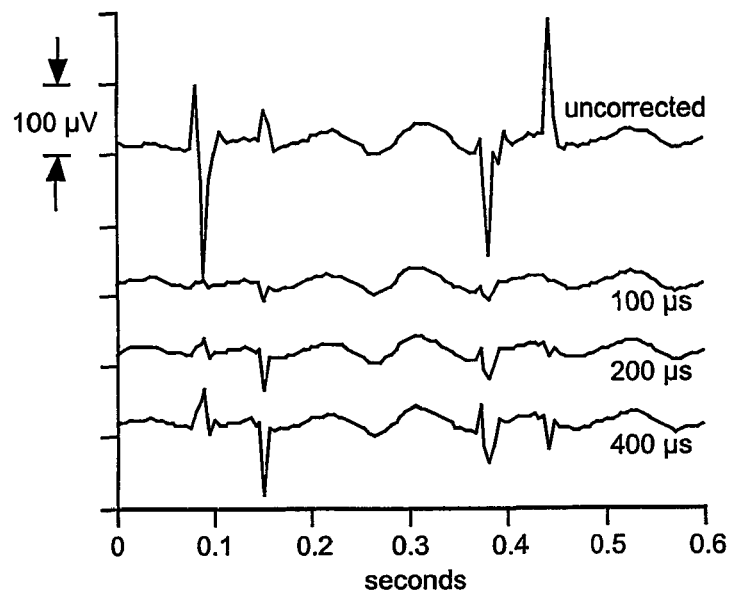
FIG. 13. Graph similar to that shown in FIG. 4, depicting a simulation that shows the effects of timing errors when sampling at 200 Hz—well below the Nyquist frequency for the gradients. The waveforms are clearly undersampled and therefore appear quite different from the prior Figure. The magnitudes of the residual artifacts, however, are very similar. The three lower curves show the artifacts that remain after correction with tiring errors of 100, 200 and 400 μs.

The efficiency of the subtraction of the gradient artifacts is effectively independent of sampling rate, and a repeated single sample, properly timed, can be used to correct for the artifact at that time point completely. This general finding is shown in FIG. 13 which shows the same effects of timing shifts at a low sampling rate of 200 Hz, well below the Nyquist rate (the gradient activity is aliased into the digitized EEG signal. As in the prior example, the magnitude of the residual artifacts increases as the sampling is delayed with respect to the scan timing. Its magnitude is no worse than that seen with more rapid sampling.

It is clear that if the sampling is timed precisely to the gradient activity, the residual errors will be eliminated much more effectively. Perhaps less intuitive is the fact that this does not require Nyquist rate sampling for the artifact frequencies. Time (phase) shift and frequency can be seen as "duals": Perfect sampling needed for artifact subtraction could be achieved by sampling at infinitely high frequency with arbitrary timing or with precise synchronization at an arbitrarily low sampling rate. To yield the same 100:1 suppression that requires 880 kHz sampling, the sample timing would require an accuracy of 1/880 kHz, or 1.14 μsec. Ideally, the residual scanner artifact should be small compared to the thermal noise of the EEG signal. With analog filtering and proper recording technique (outlined in the examples below), the scanner artifact is about ten times the amplitude of the EEG. Assuming an EEG signal to noise ratio of 100:1, a thousand-fold suppression is needed in the digital processing, achievable with either 8.8 MHz/channel sampling (which could come only at tremendous expense in the digitization hardware), or with an easily achieved 114 nsec timing accuracy

EXAMPLES

The following examples are presented to illustrate the present invention and to assist one of ordinary skill in making and using the same. The examples are not intended in any way to otherwise limit the scope of the invention.

Example 1

Acquiring Simultaneous EEG and Functional MRI

Methods

EEG Device and Lead Placement

The EEG device incorporates numerous hardware modifications to reduce artifact in concurrent EEG/fMRI, and was provided by Telefactor Corporation (W. Conshohocken, Pa.). Signal is detected from the, scalp using silver chloride plated plastic cup electrodes connected to a compact magnet-compatible local amplifier (headbox) via 10 foot carbon fiber leads with a resistance of 1 kΩ/foot. This design minimized both artifact in the MR images and the induction of RF current loops in the lead wires.

Figure 1B:
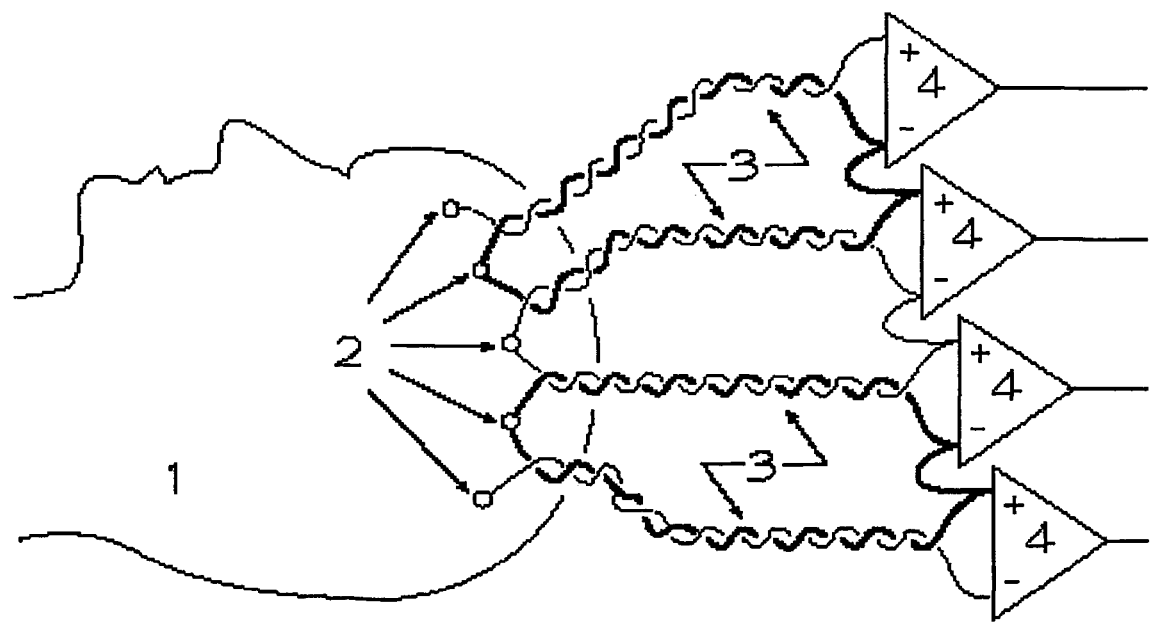

A lead configuration was devised that minimized unwanted current induction by recording EEG in a hard-wired montage using special dual lead electrodes. The lead wires from each electrode pair were twisted together over their entire length, forming a chained bipolar montage for each hemisphere (fp2-f8, f8-t4, t4-t6, t6-o2, o2-p4,p4-c4, c4-f4, f4-fp2; fp1-f7, f7-t3, t3-t5, t5-o1, o1-p3, p3-c3, c3-f3, f3-fp1). the dual leads allowed each differential pair to be twisted together (FIGS. 1A-B and FIG. 2A). The resulting configuration leaves only small loops at the head in which current can be induced. As shown in FIG. 2B, currents induced by motion and gradient switching should be self canceling, for the current induced in consecutive twists will flow in opposing directions in each lead wire.

The magnet-compatible headbox contains 32 separate channel inputs, each with a differential amplifier coupled to an RC filter having a time constant of 0.25 msec. Sixteen channels were used to record EEG, and two additional channels were used for electrocardiogram (EKG). EKG was acquired using a pair of twisted single lead electrodes placed above and below the heart on the subject's back. This placement minimized lead motion, and thus electrical artifact, due to breathing. A scan trigger channel was also used to receive a pulse from the scanner every TR to aid in post-processing of the data. The signal was filtered in all channels with a band pass of 0.5-70 Hz to further attenuate high frequency noise. A single lead was connected at cz to headbox ground as an added patient safety measure, but was not used as a montage reference.

The signal was fed to a battery powered isocoder containing an A/D converter where it was sampled at 200 Hz., and the digitized signal was carried out of the shielded magnet room via optical fiber to maintain the scanner's electromagnetic isolation. After translation to TTL, the data were routed to a Telefactor Digital EEG (D/EEG) (486 computer). The EEG data could then be viewed in real time and sent off-line via a 10 baseT Ethernet connection to a post-processing and viewing station for further artifact attenuation.

Scan Protocol

All subjects signed a consent form approved by the UCLA Human Subject Protection Committee prior to MR scanning, which was performed in a General Electric (Waukesha, Wis.) 3T scanner modified for Echo Planar Imaging (EPI) by Advanced NMR Systems. No visual or auditory stimulation was provided to the subjects during functional scanning.

Scout scans of the entire brain were first acquired to localize slice planes parallel to the AC-PC line through the occipital cortex. To acquire EEG during functional scanning, the scan protocol was then specified to allow windows of readable EEG between gradient bursts. An EPI sequence was used with TR=4000 ms, echo time (TE)=45 ms, 64×64 matrix, 20 cm×20 cm field of view (FOV), 4 mm slice thickness, and 1 mm gap to collect 6 slices spaced evenly over the TR period, leaving a 580 ms window of readable EEG between each 90 ms period of gradient induced noise (an 87% duty cyde). An EPI sequence (TR=6000, TE=54, 128×128 matrix, 20 cm×20 cm FOV) was then acquired coplanar with the functional scans for use as an anatomical reference.

Artifact Reduction Post Processing

Post-processing and viewing was performed on a Dell Inspiron 3000 Pentium PC. After importing data from the D/EEG over the wire, the EEG data was viewed with Telefactor Twin software, and processed further using home-built software described below to remove remaining artifacts. The residual artifact included both noise from e.m.f. induced by the magnetic field gradients (which appeared in the EEG when a slice is acquired) and ballistocardiogram. The latter occurred in a fairly regular pattern just lagging the Q wave of the EKG, but its morphology and amplitude differed in each EEG channel.

To suppress gradient noise and ballistocardiogram in the EEG record, the gradient noise was first removed by blanking the EEG and EKG data for the duration of each MR slice acquisition. Following a trigger every TR, the 90 ms data segments containing scan artifact were replaced with zeros. Therefore, large deflections caused by the MR gradients did not corrupt the EEG data during the averaging and subtraction in further artifact removal Next, using a method similar to that of Allen et al. (Allen, Polizzi, Krakow, Fish, & Lemieux, 1998), sections of EEG were averaged together following a cardiac trigger to yield the ballistocardiographic artifact. To identify the initiation of each cardiac pulse, a single artifact-free QRS wave segment of the subject's EKG, recorded inside the scanner when no scanning was taking place, was used as a reference (see FIG. 4A). This reference wave segment was compared to portions of the EKG data of the same number of data points as the reference segment that were shifted by one point at a time, and calculated a correlation coefficient (CC) for each data portion. When the CC exceeded an empirically selected value (typically 0.7), the peak CC following this threshold crossing was identified to trigger the initiation of ballistocardiogram averaging and subtraction.

Figure 4:
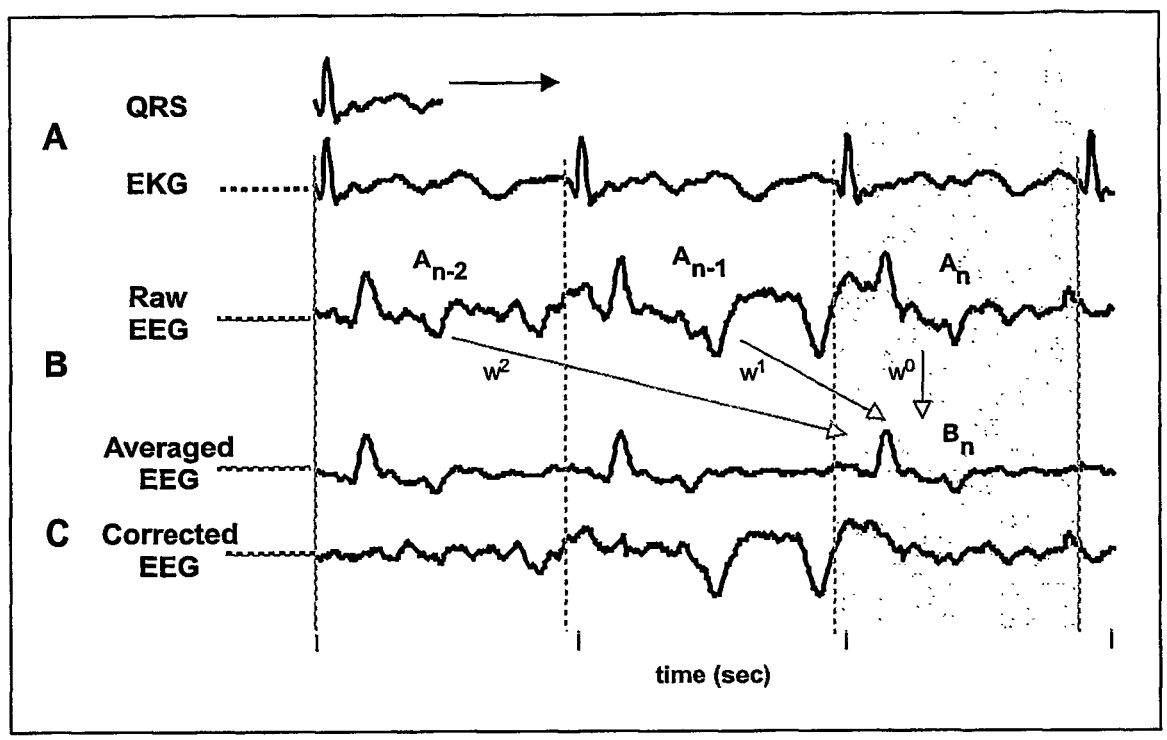
FIG. 4. Traces illustrating the ballistocardiogram subtraction algorithm, shown using data collected on a normal volunteer. A) A segment of the subject's QRS wave was correlated to their EKG, and peak correlation values initiated a trigger (shown by the vertical dotted lines). B) Trigger to trigger segments were then averaged, weighting segments less and less by temporal displacement from the nth (shaded) segment. C) The averaged data was subtracted from the raw EEG to yield ballistocardiogram-free EEG.

FIG. 4B illustrates the averaging and subtraction algorithm performed on the data in each EEG channel. Every trigger-to-trigger section of raw EEG data ($A_n$) was averaged with all preceding sections. Because EEG and EKG should be uncorrelated, this method averaged out the EEG signal and left only ballistocardiogram ($B_n$). Data sections were weighted inversely with their temporal displacement from the current sample to compensate for slow changes in the ballistocardiographic artifact, calculating the ballistocardiogram in each trigger to trigger section using the weighted average $$B_n = \frac{\sum_{i=0}^{n} w^i A_{n-i}}{\sum_{i=0}^{n} w^i}$$

with a weighting factor $w=0.9$. Thus, the earlier cycles formed an exponentially decreasing contribution with a time constant of roughly 10 sections. The averaged wave, $B_n$, calculated separately for each channel, was subtracted from that channels raw EEG, $A_n$, to yield artifact free corrected EEG.

Variations in section length due to changes in heart rate were accounted for by averaging sections point-by-point The first data point in each section was averaged with the first data point in previous sections, the second with the second, etc. Data points at the end of longer sections were averaged with corresponding points in other long sections, and the weighting factors of each point were adjusted accordingly. To avoid subtracting data with too few points averaged, the subtraction was performed only if three or more points were used in the calculation; otherwise, the raw data remained in the final record.

Characterization of Noise Reduction

Noise Reduction Due to Lead Dress: Phantom Study

To characterize noise reduction due to the twisted dual-lead dress, scanning experiments were performed using a biological phantom—a 9 pound head-sized grocery store roasting chicken—and compared twisted vs. untwisted lead arrangements. The leads were placed at distances corresponding approximately to standard international 10-20 positions on the phantom. The eight electrode chained twisted montage detailed above was placed on the left hemisphere, and on the right was placed a matching dual lead non-twisted montage. A scout scan was acquired to position the functional slices to cover the phantom. Functional EPI scans were then performed as described previously.

The EEG data were analyzed to quantify noise reduction due to the lead dress, calculating the loss, in dB, using 30 second data segments as $$dB = 20\log\frac{\sqrt{\sum V_{twist}^2}}{\sqrt{\sum V_{no\text{-}twist}^2}}$$

where averages were taken over all twisted and all untwisted channels. Gradient noise reduction was calculated by subtracting the square root of the sum of the squared voltages without scanning from that during scanning, and then calculated attenuation as above.

Noise Reduction Due to Lead Dress: Human Study

To characterize twisted lead noise reduction further, the above study was repeated on a 25-year-old normal male volunteer. Again, the chained twisted lead set was placed on the subject's left hemisphere, and the untwisted set on the subject's right The subject's EEG was recorded inside the MR scanner, both with and without scanning.

Spectral Analysis

By restricting the timing of the EPI acquisitions to fall outside of the frequency band of interest for EEG (e.g., to study alpha activity, the scanning rate must be less than four images/second), it was possible to retain useful EEG spectral information. To illustrate this, the 25-year-old normal volunteer was scanned during three different tasks known to moderate alpha power—a basic eyes open/eyes closed task, a math task, and a visualization task. All studies were performed during functional MRI as described above. A baseline eyes open scan was acquired, and then the three tasks were run as follows.

In the eyes closed task, the subject was given verbal cues during the scan to keep his eyes open for the first two minutes, closed the next two minutes, then open for the last minute. For the next two tasks, the subject was told to keep his eyes dosed First, the subject was instructed to count backwards by sevens from the four digit number given to him two minutes into the scan. To verify that the task was performed, the subject was asked for the number he ended on after the three minutes of counting. Second, the subject was instructed to visualize eating his favorite meal, again two minutes into the scan.

After post-processing the EEG to remove artifact, the alpha power in each TR was calculated using software developed in house. With this software, the EEG power in user-defined bands with each TR was found using the Fast Fourier Transform. Spectral power in the alpha band was used as a reference function to calculate fMRI signal maps.

Results

Noise Reduction Due to Lead Dress: Phantom Study

Figure 5:
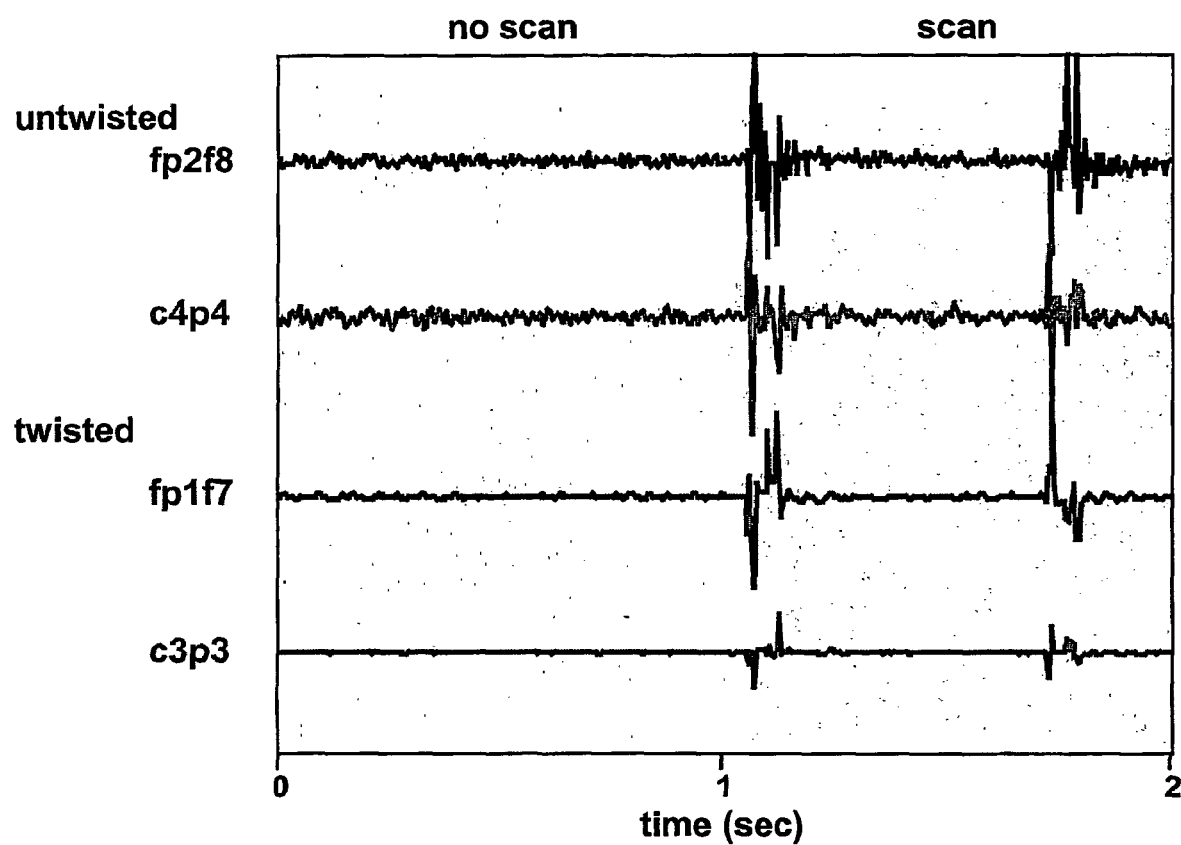
FIG. 5. EEG of a phantom recorded inside the MR scanner using twisted and untwisted leads, showing recordings both in absence of scanning and during EPI. With or without scanning, EEG recorded using the untwisted leads was significantly noisier.

EEG recorded on the phantom using the untwisted leads was substantially noisier than that recorded using their twisted counterparts. FIG. 5 shows the recorded EEG in both twisted and untwisted lead channels. When not scanning, the twisted leads reduced random noise power by an average of 5.4 dB. During scanning, gradients caused large artifacts in both the twisted and untwisted lead sets, but this noise power was reduced by an average of 6.3 dB in the twisted leads.

Twisted vs. Untwisted Leads on a Volunteer

Figure 6:
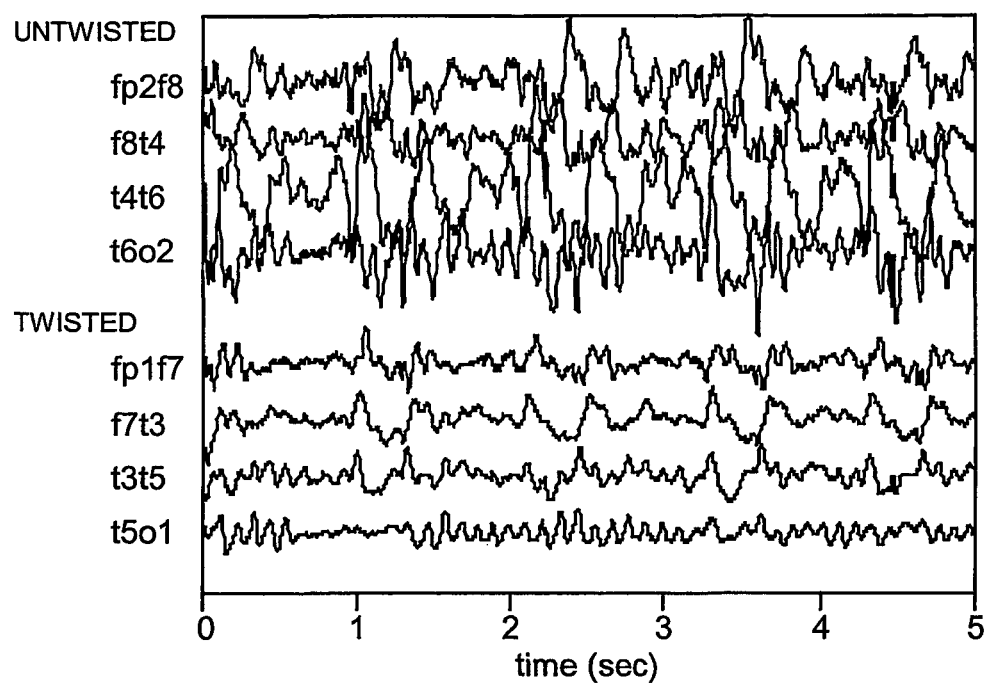
FIG. 6. Raw EEG of a normal volunteer recorded inside the MR scanner using untwisted (top) and twisted (bottom) leads. EEG recorded with the untwisted leads was significantly noisier. Ballistocardiogram is visible in the twisted lead data, but is reduced compared to the untwisted leads.

FIG. 6 shows EEG data recorded on a normal volunteer inside the scanner when no scanning was taking place. Twisting the leads (shown here on the left hemisphere vs. the untwisted on the right hemisphere) reduced noise by an average of 7.5 dB across all channels.

Noise Reduction Due to Artifact Post-Processing

Figure 7:
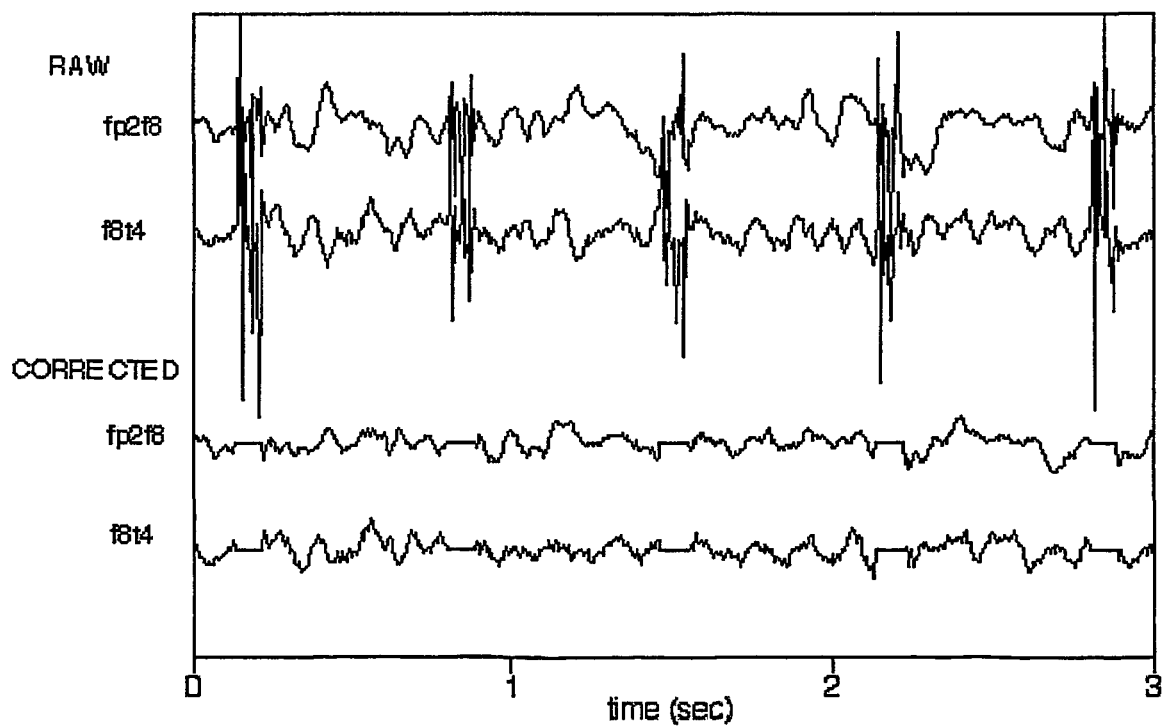
FIG. 7. EEG recorded on a volunteer during fMRI, before (above) and after (below) post-processing to remove the ballistocardiogram.

FIG. 7 shows EEG recorded on a volunteer during functional MRI before and after post-processing. The post-processing removed significant gradient and RF artifact, as well as ballistocardiogram.

Spectral Data

Figure 8:
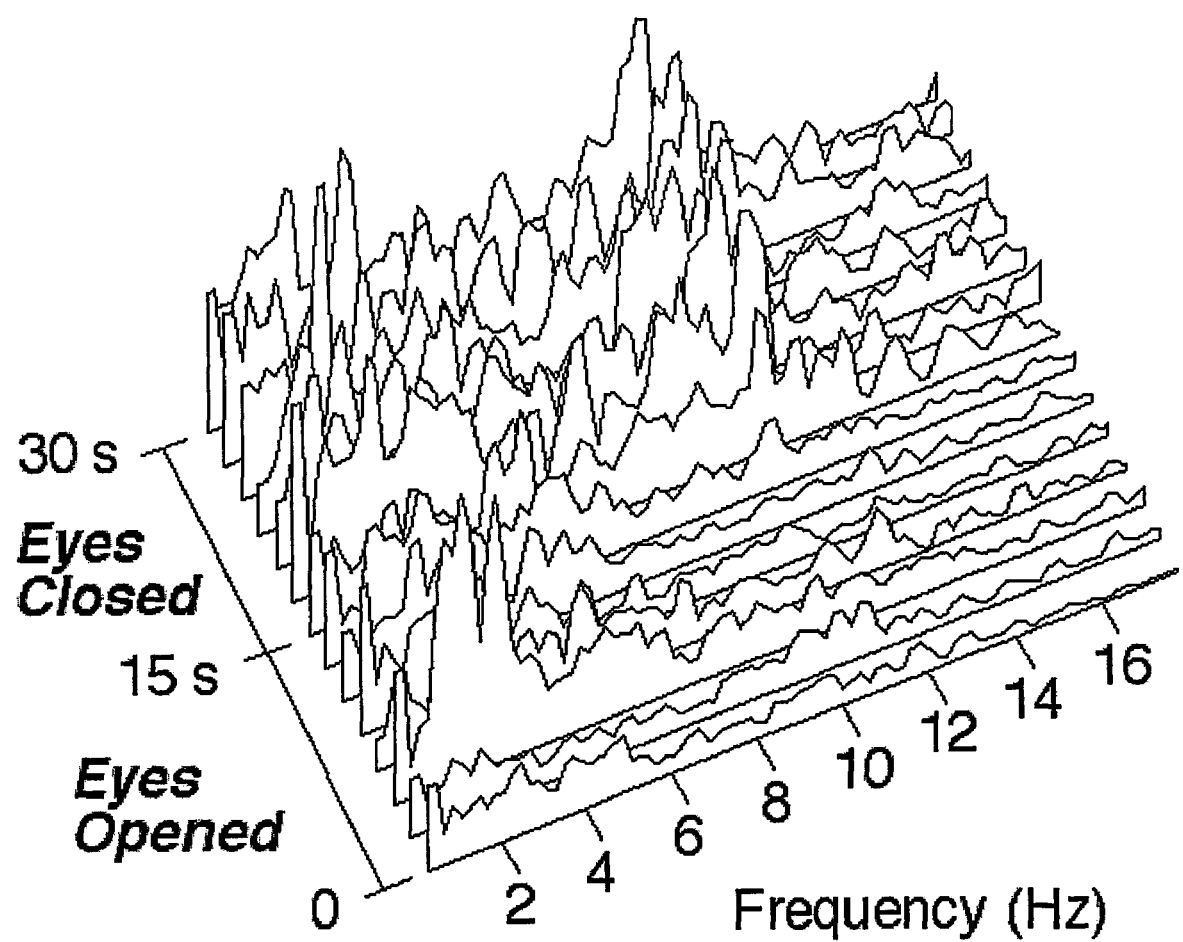
FIG. 8. Power spectrum of EEG recorded simultaneously with fMRI, in steps equal to the TR of 2.5 seconds, showing expected increases in the alpha band (8-12 Hz) when the subject's eyes were closed FIG. 9. Graph depicting how errors in gradient noise cancellation will occur when the sampling and gradient activity are asynchronous. In this Figure, the sampling used to create an error estimate (open circles) has drifted by approximately 200 μs compared to the current sample (closed circles). Subtracting the error estimate actually increases the residual error (by more than 17%), as indicated by diamonds.

The data shown in FIG. 8 was recorded on a normal volunteer during an eyes open, eyes closed paradigm using simultaneous EEG/fMRI. Here, four slices were acquired with a 2.5 second TR. When the subject's eyes are closed, power in the alpha band, between 8 and 12 Hz, increases significantly. And as is expected, this alpha signal is not present when the subjects eyes are open.

Discussion

Using a combination of analog pre-preprocessing and digital post-processing, this method allows one to record clean EEG during functional MR scanning. While the EEG is obscured during gradient bursts, it recovers quickly after each slice acquisition. With this method, then, a trade off must be made between brain coverage in functional scanning and the fraction of useable EEG in the data record. Consideration must also be given to the timing of slice acquisition so that it does not overlap with desired spectral frequencies.

The invention provides a potentially powerful tool for localizing the sources of various EEG waveforms. Because the EEG is acquired simultaneously with fMRI instead of serially, it can be used as a direct source for the fMRI reference function. In this way, activation maps could be made of any relevant changes in the EEG: spike and slow wave patterns in epilepsy, spectral changes, or even event related potentials.

Example 2

Method for Removal of Artifacts in Simultaneous EEG and fMRI

The strategy outlined below is applicable to any method involving digital subtractive noise cancellation, including EEG, EEG/fMRI, as well as any environment in which subtracted averages of artifacts are used to reduce noise.

Methods

EEG Recording and Electrode Placement

The basic approach of differential recording has been described previously (Goldman, Cohen et al. 2000; Goldman, Stern et al. 2000). Paired silver electrodes are placed on the scalp surface attached with conductive electrode gel and check to ensure that the nominal impedance is less than 5 k$\Omega$ for each electrode. The electrodes are themselves attached to two carbon fiber conductors having a distributed resistance of approximately 3 k$\Omega$/m The wires are dressed in pairs with the leads from adjacent electrodes twisted together tightly to minimize electromagnetic pickup. This configuration offers about 6 dB attenuation of artifacts from gradient and ballistocardiographic noise sources (Goldman, Stern et al. 2000).

Amplification

Further improvements in the overall performance of in-magnet EEG can be achieved through the use of better analog electronics. Although the ballistocardiogram contains substantial energy in the range of most interest to clinical EEG (from 1 to 50 Hz), the other main sources—gradient noise and RF transmit noise—have much higher fundamental frequencies. In a typical scanner, for example, the overwhelming majority of the gradient-related noise is at a fixed frequency of 1400 Hz, with significant energy distributions down to 100 Hz or less. The radio frequency energy, of course, is at radically higher frequencies well outside of the interesting pass band for EEG.

Disclosed herein is a very simple circuit that corrects for much of the analog portions of the artifact FIG. 14). An initial gain stage features a single pole filter to attenuate the large RF signals prior to sampling and provides enough gain to bring the EEG signal into the mV range without the artifacts causing saturation. The next stage offers 30 dB/octave attenuation at a corner frequency of 200 Hz (so that gamma range EEG is readily passed.)

The AC coupling problem is handled in the final amplification stage, which is arranged to include a resettable offset-nulling circuit that stores any DC offset across a low-leakage capacitor. The offset nulling switch can be, e.g., a mechanical switch, or, so that the nulling can be performed under digital control as needed, presumably when the software detects that the signal is close to digital saturation, a CMOS switch. One can reduce this design to use with a pc and assemble a single channel of this system. Under lab test conditions, the circuit is able to hold the DC offset to within 1% for 10 minutes at a time, easily meeting the system requirements for MR scanning.

The AC coupling problem is handled in the final amplification stage, which is arranged to include a resettable offset-nulling circuit that stores any DC offset across a low-leakage capacitor. The offset nulling switch can be, e.g., a mechanical switch, or, so that the nulling can be performed under digital control as needed, presumably when the software detects that the signal is dose to digital saturation, a CMOS switch. This design has been reduced to printed circuitry and a single channel of this system has been assembled. One can reduce this design to use with a personal computer and assemble a single channel of this system. Under lab test conditions, the circuit is able to hold the DC offset to within 1% for 10 minutes at a time, easily meeting the system requirements for MR scanning.

Imaging

Presented herein are examples of activation mapping data from two subjects (one each for the raw EEG data and for the EEG energy maps). Both subjects were without neurological or radiological abnormalities as assessed by a brief neurological inventory based on a form developed by the National Institutes of Health NIH and a neurological inventory performed by a board-certified neurologist. Beyond lying in the magnet during scaring with eyes closed, the subjects performed no explicit cognitive task.

All scanning was performed on a General Electric (Waukesha, Wis.) 3.0 Tesla Signa® scanner modified by Advanced NMR Systems (Wilmington, Mass.) for high performance echo-planar imaging (Brady, Cohen et al. 1991; Cohen, Kelley et al. 1996). For testing of artifact rejection, a 19 slice echo-planar data set was collected with a TR of 3 seconds, TE=45 ms, 4 mm slice thickness and 3.125 mm in-plane resolution (64×64 scan matrix and 20 cm FOV), to achieve appropriate weighting for "BOLD" contrast effects (Ogawa, Lee et al. 1990a). For the mapping data, after image-based shimming (Reese, Davis et al 1995) and collection of a scout scan, imaging was performed using a gradient echo EPI scan as described above. These data, however, were acquired with a longer TR of 4 seconds and only four slice planes. The pulse sequence was modified to include a 5 µs trigger pulse at the beginning of each TR period, the leading edge of which was used for synchronization of the EEG sampling acquisitions.

Digitization of the EEG

EEG data are acquired using a PCI-1200 National Instruments, Houston, Tex.) on a pc-compatible microcomputer. Using LabView (National Instruments, Houston, Tex.), sampling software was developed that responds to the leading edge of the scanner trigger by acquiring a fixed number of samples at a user-specified rate. Specifically, with a TR of 3 seconds, one can acquire 599 samples at a rate of 200 Hz following each trigger. These data are immediately flushed to a file in a background process; to accommodate this process one sample point is dropped with each TR.

Averaging and Artifact Removal

A frame of EEG data is collected from each channel with each scan TR, and the frames are averaged separately for each channel to create an accurate representation of the scanner artifact One can then remove the artifact by simply subtracting the averaged signal from its respective channel. The next step is to manually inspect the EEG data for characteristic artifacts, such as eye blink and facial muscle movement that are recognized easily by their morphology within and across channels.

Ballistocardiogram Suppression

Details of the ballistocardiogram suppression procedures have been published previously by Goldman et al., (Goldman, Stern et al. 2000) and will only be summarized here briefly. Because the cardiac-induced motion is nearly repeated with each heartbeat, the resulting artifact is essentially the same and is superimposed onto the desired EEG. To remove this artifact one can detect the heartbeat using the electrocardiographic signal and calculate the average ballistocardiogram over many heartbeats. One can then subtract this average from the EEG signal. Of course, the morphology of the ballistocardiogram differs in each of the EEG channels as the motion of each lead differs slightly. Therefore this averaging and subtraction process is preferably performed separately for each of the EEG lead pairs. The method is conceptually like that described by Allen et al., (Allen, Polizzi et al. 1998) but differs in the details by which slow variations in the ballistocardiogram are accommodated.

Image Processing

Using software developed in-house, standard FFT methods were used (Press, Vetterling et al. 1992) to determine the power separately in five different spectral bands in the EEG signal for each TR period. Following convention, data were combined from 0.5 to 4 Hz ("delta"), 4 to 8 Hz ("Theta"), 8-12 Hz ("Alpha"), 12 to 30 Hz ("Beta") and from 30 to 4 Hz 70 Hz ("Gamma"). Using this model of spectral energy as a function of time, one can then estimate a prediction of the BOLD signal changes by convolution of the spectral data with an a priori model of the brain hemodynamnic response function (Cohen 1997). The convolution introduces a lag in the time course that is thought to represent a reasonable estimate of the hemodynamic latencies and, in addition, acts as a low pass filter, which tends to reduce somewhat any noise in the EEG data (see FIG. 17).

One can then use scanSTAT (available via the Internet at the URL for the UCLA Brain Mapping Center, http://www.brainmapping.org) to first spatially filter the images and then to form statistical maps indicating the correlation between the EEG spectral power in each band and the local fluctuations in MR signal intensity. The convention is to indicate regions of increasing positive correlation in colors from red to yellow and areas of increasing negative (anti) correlation in colors from blue to cyan. In particular, regions of high negative correlation are interpreted as indicating decreased blood flow and metabolic activity.

Results

Gradient Artifact Suppression

Figure 15:
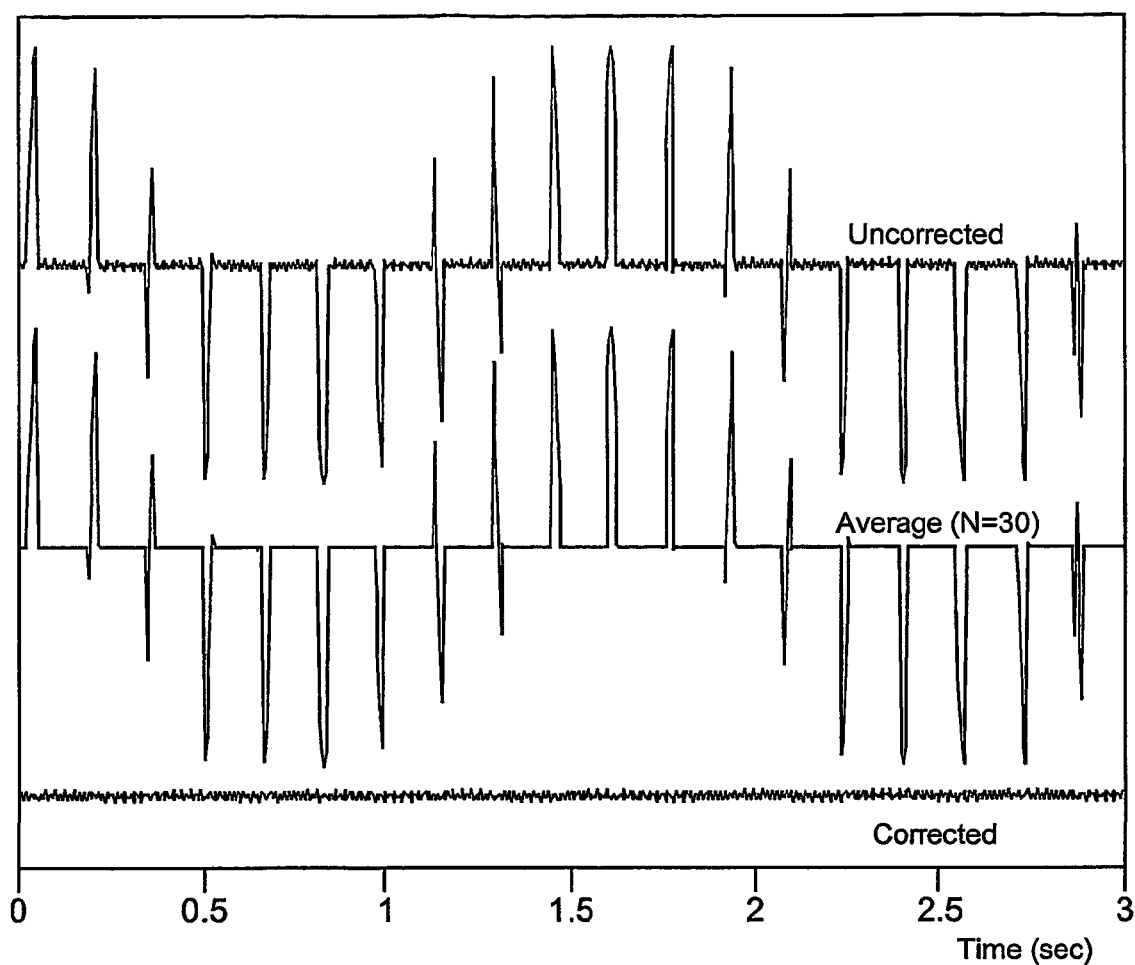
FIG. 15. MR gradient activity recorded with triggered 200 Hz sampling using a 3 s repetition time (TR) and nineteen slices. The uncorrected signal is shown at top for a single TR. In the middle is shown the average of 30 TR periods, and at bottom, the difference between the uncorrected and averaged signals ("corrected").

Tested was the principle method of triggered sampling by recording the analog waveform that drives the gradient coils, to determine the efficacy of the method independent of physiological signal fluctuations. The uncorrected signal from a single channel appears in FIG. 15 (top). Then calculated was the average of 30 repetitions to produce a representation of the gradient activity. The averaging process removes noise uncorrelated with the imaging gradients. Finally, this averaged signal was subtracted from the uncorrected signal, yielding the corrected signal appearing in the lower portion of FIG. 15. After correction, the large amplitude gradient activity is removed completely and all that remains in the signal is the small, uncorrelated, noise fluctuation.

Figure 16:
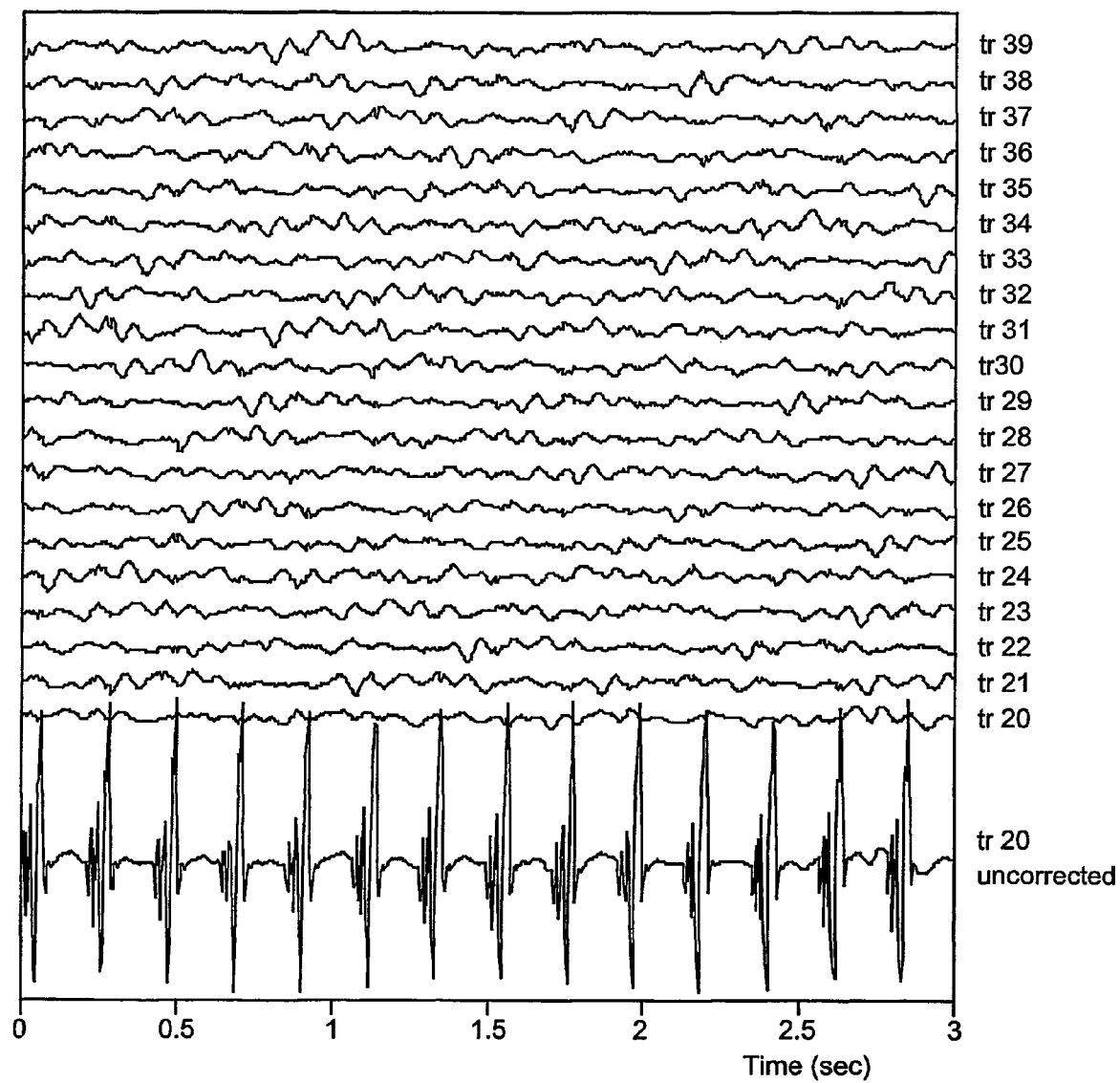
FIG. 16. Human EEG data collected during echo-planar functional imaging. The uncorrected data appear at bottom. Above them are corrected records from twenty successive TR periods.

The echo-planar imaging gradient artifact, which lasts for 23 ms and goes through 32 sinusoidal oscillations in that period, is sampled with only four data points for these data. The digitized waveform is thus a very crude record of the actual gradient activity—well below the Nyquist frequency. In addition, the morphology of the gradient waveform is grossly different for each of the nineteen slices that ate acquired in this TR period. This is due to the fact that the digitization is phase shifted slightly with respect to the readout of each slice location. There is also no amplifier "ring down" following the gradient pulses, as there is no high pass filter on the amplifier input A similar experiment was performed, recording electrical potentials from the human scalp with a single differential electrode pair. Once the subject was placed into the imaging system, the scanning protocol was similar to that used above: fourteen slice locations with a 3 second tr. As acquisition of each slice requires approximately 38 msec of gradient activity, the gradients can be expected to obscure about 20% of the EEG record. As a consequence of several system non-idealities (such as the small inductance of the EEG leads, there will still be some electrical "ring-down." FIG. 8 (bottom) shows 3 s of the EEG record during scanning, sampled at 200 Hz and triggered by the scanner. Prominent gradient artifacts are present even after low pass filtering. FIG. 16 also shows a series of 20 successive 3 second traces after gradient artifact correction.

EEG Energy Mapping

The subject was scanned while he lay prone in the magnet with his eyes open. The raw EEG data were processed as outlined above, first blanking the gradients and then removing the ballistocardiogram. The data were then submitted to a Fourier analysis and the energy at each of five pre-defined frequency bands was determined for each TR (that is, for each image time point). For each frequency band, therefore, it was possible to generate a separate time course.

Figure 17A:
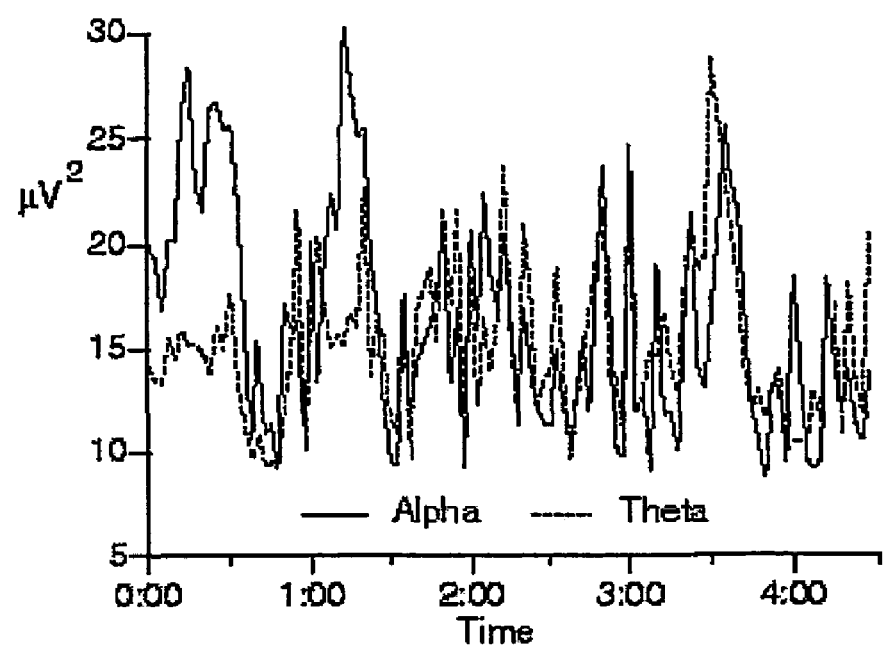
FIG. 17A. Graph showing energy as a function of frequency and time, derived from EEG data acquired during scanning.
Figure 17B:
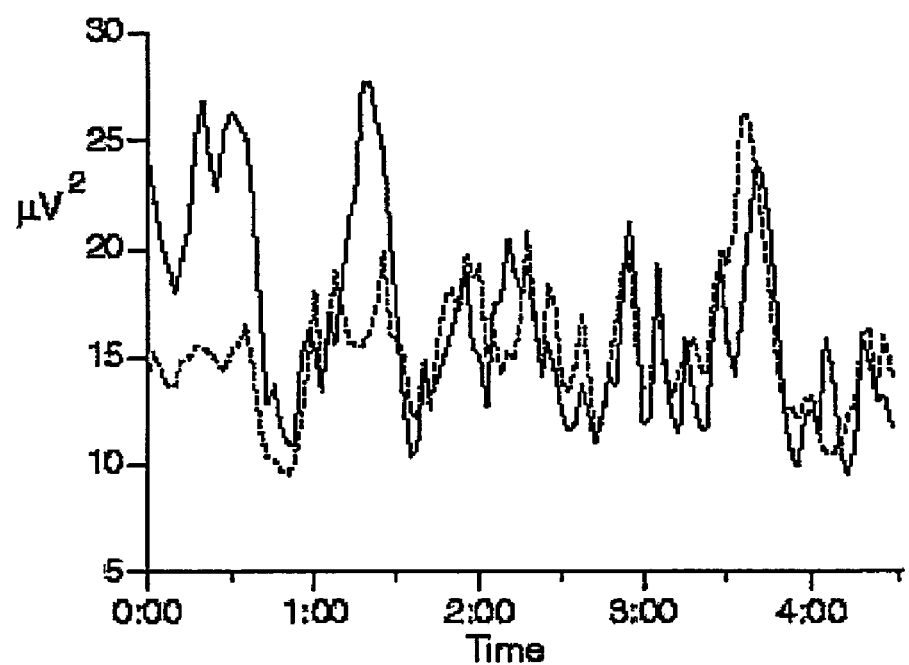
FIG. 17B. Graph showing estimated fMRI activation time course for the EEG data appearing in FIG. 9A. For clarity, only the Alpha (solid line) and Theta (dashed line) bands are shown.

Shown in FIG. 17A is the energy as a function of time in the alpha and theta bands for a four and a half minute period while the subject was at rest. The energy levels in these bands are largely independent for the first minute and a half of this session and seem to co-vary for the latter portion of the recording. FIG. 17B demonstrates the estimated time course of the BOLD signal response based on the (untested) assumption that the hemodynamic response related to the EEG is similar to that seen in activation studies (e.g., (Cohen 1997; Cohen and DuBois 1999)).

Figure 18A:
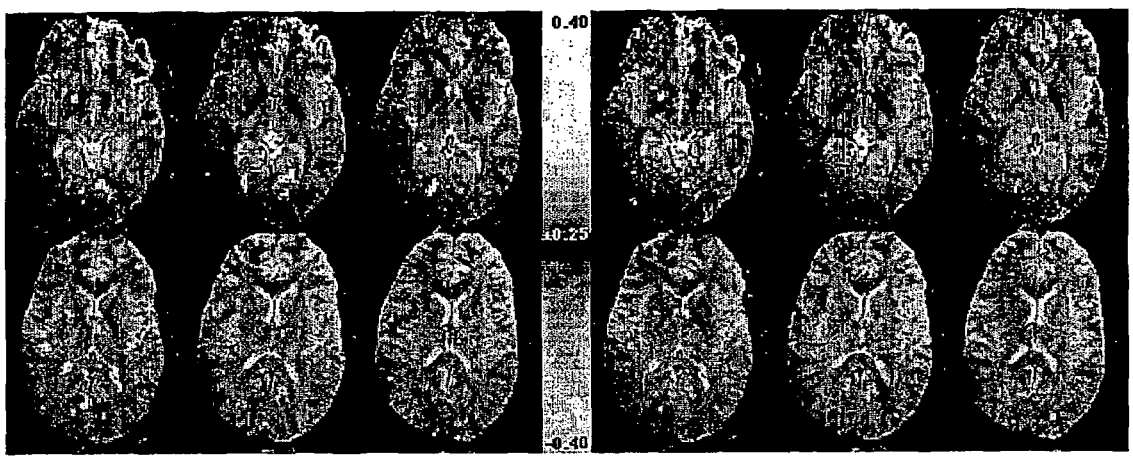
FIGS. 18A-C. Functional MRI statistical maps of signal change correlated with spectral energy at each of five frequency bands (18A left, Delta; 18A right, Theta; 18B left, Alpha; 18B right, Beta; 18C, Gamma), expressed as coefficient of correlation. Note that the color scale for the lower frequencies (18A) is different, as the correlations were overall lower. All five images were calculated from the same 4:30 (min:sec) acquisition taken with the subject at rest with eyes open.
Figure 18B:
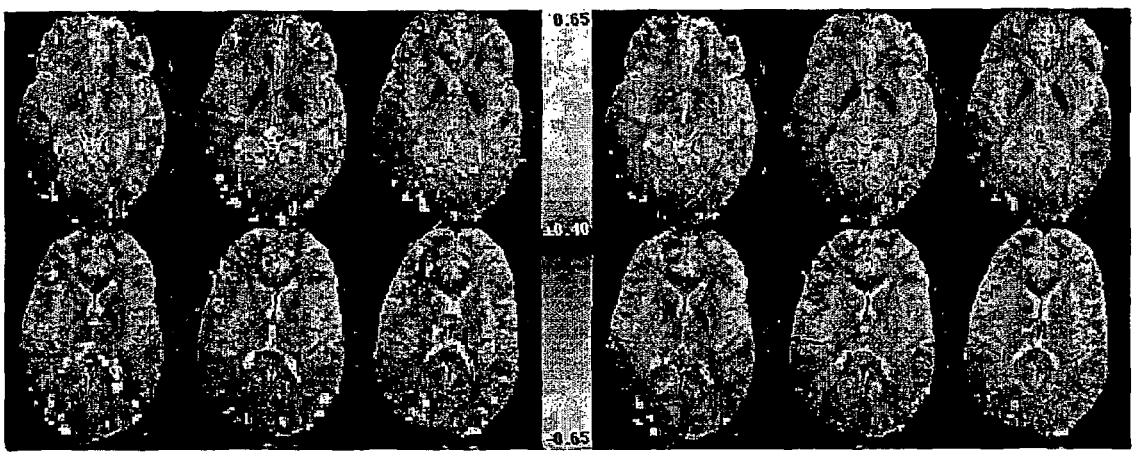
Figure 18C:
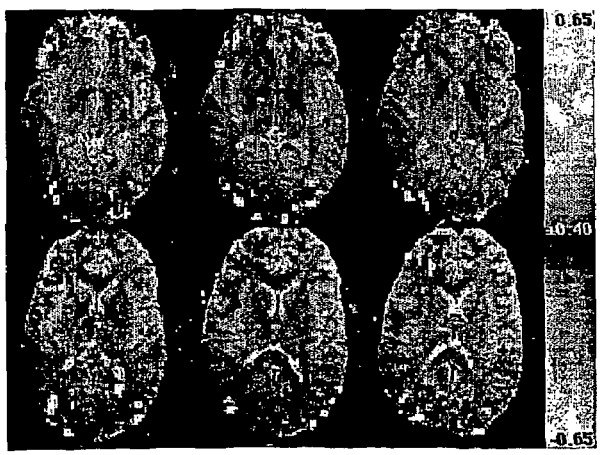

Using the latter as a reference function, then calculated were correlation maps for each pixel location with the energy intensity in each previously defined frequency band using scanSTAT. The images were first subjected to a simple 9 pixel smoothing to reduce pixel noise. The resulting brain maps are shown in FIGS. 18A-C, with a separate map for the pixel correlation with each of the frequency bands. The images are remarkable in showing very high correlations, little artifactual activation in white matter or CSF, and substantial symmetry, all of which suggest that the artifact content is low. Note also that the signal intensity in extrastriate areas shows a substantial signal decrease with increases in alpha level.

CONCLUSIONS

While there have been numerous obstacles to the fusion of functional MRI and electroencephalographic data, the purely technical challenges of eliminating the cross contamination of the recorded signals seem to have yielded to rather straightforward engineering solutions of somewhat surprising simplicity. The tools outlined here are all both easy to construct and made from inexpensive components. The complete software solution can be made to run as a standalone unit using the LabView programming environment. The availability of high quality integrated instrumentation amplifiers such as the INA114 from Texas Instruments Corporation (FIG. 14) makes the analog engineering uncomplicated as well.

Certain factors affect the extent to which the data can be interpreted accurately. For example, the energetics of the spectral EEG signal are themselves largely unknown. Some components, such as the theta rhythm, have long been suspected to be driven by subcortical generators and might plausibly be associated with increased thalamic activity reflected as an increase in blood flow. The alpha rhythm, however, may well be intrinsic to the cerebral cortex (though influenced by thalamus) and is often interpreted as a sort of cortical testing state. What is clear, however, is that by continuing to study the relationship between scalp (and presumably brain) electrical potentials and magnetic resonance signal intensity (presumably indicating increases or decreases in cortical blood flow) it should be possible to understand better the physiological basis of the electroencephalogram (Schomer, Bonmassar et al. 2000).

The signal processing methods developed to solve the problems in simultaneous EEG and fMRI have a broad range of additional applications. For example, these methods can be used, without modification, to study electrical evoked potentials (Bonmassar, Anami et al. 1999) and their localization or, conversely, to yield a better temporal of the "single-trial" evoked MR response (Buckner, Bandettini et al. 1996). The clinical applications of fully integrated fMRI and EEG are substantial, the most immediate harvest will likely be in seizure source localization as an adjunct to other diagnostics used in surgical planning (Engel 2000). Intetictal spikes are a common finding in the epileptic brain yet even when recorded from the cortical surface do not provide definitive and reliable source localization. Recently, however, fast ripples have been reported in rat models and in the epileptic human brain, that are associated closely with seizure foci (Bragin, Wilson et al. 2000). A still speculative interpretation is that such activity represents rapid spontaneous action potentials that are ultimately propagated and observable as intetictal spikes. If so, this gives added hope to the idea that localization by fMRI of interictal spikes might become a reliable means to plan resective brain surgery, as has been proposed already by several others (e.g., (Warach, Levin et al. 1994; Warach, Ives et al. 1996; Allen, Polizzi et al. 1998; Ramabhadran, Frost et al. 1999; Hoffmann, Jager et al. 2000)).

Although EEG recorded during MR imaging is particularly noisy, most of the artifacts contended with here are present in conventional EEG, though at lower amplitude. For example, the activity of the heart, particularly the electrocardiogram, is a contaminant that can be corrected in the same manner as the minimization of the ballistocardiogram. AC line noise is often present as well, and could be eliminated by using a triggered sampling approach, timing each block of samples to the power line oscillations—these could be detected readily with a phase-locked loop.

Digital sampling based on precise synchronization with well characterized noise sources (i.e., triggering on the basis of scanner gradient timing) has applications that extend well beyond Magnetic Resonance Imaging. It is clear, for example, that a comparable approach could be used to remove noise sources associated with AC power line oscillations; these include the removal of "hum" from digitally processed audio, light flicker from fluorescent illumination, and other contaminants of digitally sampled signals.

Example 3

Increasing Dynamic Range Available in Digitized Electro-Encephalographic Signals The scalp electrical potentials used in the EEG contain both time varying and static (DC) components. Often the DC offset is much larger than the EEG, but it is seldom of interest for clinical diagnostic purposes, as it contains essentially no information. However, it does cause trouble as it increases the dynamic range needed to digitize the EEG signal. For example, the EEG may be only a few microVolts ($\mu V$), while potentials of several tens of milliVolts (mV) may exist between electrodes, or as a result of the chemical electrode potential developed when the electrode is in contact with the scalp. The depth of the signal digitization will be reduced by the ratio of the EEG to the DC potential: assuming a DC offset of 10 mV, an EEG signal of 10 $\mu V$, and a 12 bit analog to digital converter (ADC), the 4096 different levels representable by the ADC will be reduced to only 4 levels for the EEG. Clearly this is unacceptable, as the quantization noise will dominate the recordings.

For this reason, conventional EEG amplifiers are equipped with AC-coupled (high pass) inputs, usually a capacitor separating the output of the first stage amplifiers from the input to the ADC. As the frequencies of interest in EEG can be quite low, the inputs will typically have time constants of several seconds, allowing fluctuations of 1 Hz or so to pass without significant attenuation. One consequence of this AC coupling is that it creates a time constant for signal recovery if the input saturates and, because these filters must pass very low frequencies, the settling time for the analog signal to come back to the center of its nominal range can be quite long. For conventional EEG recordings this is acceptable, as large DC shifts are not frequent.

In fMRI, the recovery time associated with AC coupling is a particular problem, as the gradient-induced artifacts can be large enough to bring the input stages into saturation. When this occurs, the amplifiers that follow can be pinned at either the positive or negative supply rails for several milliseconds. When the gradients cease, the amplifiers may require significant settling time such that the gradient artifact substantially outlasts the gradient event A recent report for example, from Lovblad, et al., reported that even when using a reduced gradient activity BURST (Hennig and Hodapp 1993) sequence, "The EEG could not be interpreted during the artifact caused by the excitation pulse, but the recording becomes readable in less than 1 second (approximately 100 msec) after completion of the BURST" (Lovblad, Thomas et al. 1999). Thus, if they were to use, for example, an eight slice acquisition with a 2 second TR (repetition time), the EEG signal would be obscured more than half of the time by either gradient activity or amplifier recovery.

To remove the DC offset, and to reject saturation problems, the invention provides a circuit that behaves as illustrated in FIG. 19.

In this circuit, the high frequency common mode artifacts typically present in EEG recorded in the MRI environment are first attenuated using passive components before being differentially amplified. The differential amplification further reduces common mode artifacts. The data are then presented to a high pass ("anti-aliasing") filter to both attenuate the artifacts and to minimize the possibility of aliasing in analog to digital conversion. The final stage of this circuit performs the dual role of amplifying the signal further and removing any DC bias. This is done by comparing the signal differentially to a DC reference value sampled from the signal itself. The sampled signal is stored under a command here shown diagrammatically as a switch connected to ground.

FIG. 14 shows one preferred implementation, in which the first high pass filter consists of a resistor-capacitor (RC) network 20. The first differential amplifier is an integrated instrumentation amplifier 28. The active high pass filter is a 24 dB Butterworth filter. The sample/hold circuit 24 stores the DC signal as charge across a low-leakage capacitor 37 with a compensation circuit for the non-zero input offset current found in the amplifier that drives it The final differential stage is a standard operational amplifier 34.

With more specific reference to FIG. 14, a pair of electrodes is connected to the differential input amplifier stage 20, bypassed at high frequencies by parallel capacitance. The input amplifier 28 itself may be an integrated circuit, such as an INA114 from Burr-Brown corporation. A pair of matched 5 megohm resistors supply bias current to the integrated circuit. The output from the amplifier is used as an input to a sample and hold stage 24, which utilizes an integrated circuit 36 such as the LF398 from National Semiconductor corporation, which stores the DC voltage across a capacitor 37. A series resistance of 200 kΩ provides a time constant of 5 seconds to the sample and hold stage. The output of the sample and hold stage is applied to the offset reference pin of the differential amplifier component An offset trim adjustment 40 is provided to adjust for small static DC offsets in the integrated circuit 36. An input 39 is provided to sample and hold device 36.

The DC corrected output is presented to the input of a low pass filter 22, that utilizes operational amplifier integrated circuits 30 and 32, such as the TL072 from Texas Instruments corporation. With the component values indicated in FIG. 14, the low-pass filter is implemented in a Chebyshev configuration to provide approximately 30 decibels/octave of attenuation at frequencies above the selected pass band. A final gain stage 26 includes a gain trimming adjustment 38 to match the gains across channels.

Example 4

Further Reduction of Sensitivity to Electrical Interference from Ongoing Scanning Activity In an additional preferred embodiment, diagrammed in FIG. 20, the differential recording input stages are supplemented by a shield driver circuit that further reduces the sensitivity to electrical interference from the ongoing scanning activity, or other common mode signals in the leads. In this embodiment, the output from the initial amplifiers is coupled through an isolation amplifier to reduce the possibility of circulating currents from the RF pulses saturating later components of the amplifiers (FIG. 20). The DC offset signal is first detected digitally, then held in a digital latch, and returned via a digital to analog convertor as an offset correction. This offset correction is also coupled through an isolation amplifier. In this embodiment, the analog output is coupled optically through the RF shielded room to minimize any problems of corruption of the MR signal through factors such as ground loops. Provision is made for the recording of multiple channels of EEG data through the use of multiplexing circuitry.

REFERENCES

Abraham H D and Duffy F H (1991) Computed EEG abnormalities in panic disorder with and without premorbid drug abuse. *Biological Psychiatry;* 29(7): 687-90.

Achor L J and Starr A (1980a) Auditory brain stem responses in the cat I. Intracranial and extracranial recordings. *Electroencephalography and Clinical Neurophysiology;* 48(2): 154-73.

Achor L J and Starr A (1980b) Auditory brain stem responses in the cat II. Effects of lesions. *Electroencephalography and Clinical Neurophysiology;* 48(2): 174-90.

Adrian E D and Matthews B H C (1934) The Berger rhythm: potential changes from occipital lobes in man. *Brain;* 57: 355-385.

Allen P J, Josephs O and Turner R (2000) A method for removing imaging artifact from continuous EEG recorded during functional MRI [In Process Citation]. *Neuroimage;* 12(2): 230-9.

Allen P J, Polizzi G, Krakow K, Fish D R and Lemieux L (1998) Identification of EEG events in the MR scanner:

the problem of pulse artifact and a method for its subtraction. *Neuroimage;* 8(3): 229-39.

Alvarez X A, Lombardi V R, Corzo L, Perez P, Pichel V, Laredo M, et al. (2000) Oral Cerebrolysin enhances brain alpha activity and improves cognitive performance in elderly control subjects [In Process Citation]. *Journal of Neural Transmission Supplement;* 59: 315-28.

Bauer L O, Gross J B, Meyer R E and Greenblatt D J (1997) Chronic alcohol abuse and the acute sedative and neurophysiologic effects of midazolam. *Psychopharmacology (Berlin);* 133(3): 293-9.

Benca R M, Obermeyer W H, Thisted R A and Gillin J C (1992) Sleep and psychiatric disorders. A meta-analysis. *Archives of General Psychiatry;* 49(8): 651-68; discussion 669-70.

Berger H (1929) Über das Elektroenzephalogramm des Menschen. *Arch. Psychiatr. Nervenk;* 87: 527-570.

Berger H (1930) Über das Elektroenzephalogramm des Menschen II. *J. Psychol. Neurol.;* 40: 160-179.

Bonmassar G, Anami K, Ives J and Belliveau J W (1999) Visual evoked potential (VEP) measured by simultaneous 64channel EEG and 3fMRI. *Neuroreport;* 10(9): 1893-7.

Brady T J, Cohen M S, Weisskoff R M and Rosen B R (1991) Equipment requirements to facilitate contrast-enhanced MR imaging. *Magnetic Resonance in Medicine;* 22(2): 273-9.

Bragin A, Wilson C L and Engel J, Jr. (2000) Chronic epileptogenesis requires development of a network of pathologically interconnected neuron clusters: a hypothesis. *Epilepsia;* 41(Suppl 6): S144-52.

Braun A R, Balkin T J, Wesensten N J, Gwadry F, Carson R E, Varga M, et al. (1998) Dissociated pattern of activity in visual cortices and their projections during human rapid eye movement sleep. *Science;* 279(5347): 91-5.

Buchsbaum M S, Mendelson W B, Duncan W C, Coppola R, Kelsoe J and Gillin J C (1982) Topographic cortical mapping of EEG sleep stages during daytime naps in normal subjects. *Sleep;* 5(3): 248-55.

Buckner R L, Bandettini PA, O'Craven K M, Savoy R L, Petersen S E, Raichle M E, et al. (1996) Detection of cortical activation during averaged single trails of a cognitive task using functional magnetic resonance imaging [see comments]. *Proceedings of the National Academy of Science USA;* 93(25): 14878-83.

Caton R (1875) The electric current of the brain. *The British Medical Journal;* 2: 278.

Cezayirli S E, Little S C and Estock R (1975) Correlation of drug abuse, psychiatric diagnosis and EEG findings. *J Med Assoc State Ala;* 44(11): 616-21.

Chiappa K H, Gladstone K J and Young R R (1979) Brain stem auditory evoked responses: studies of waveform variations in 50 normal human subjects. *Archives of Neurology;* 36(2): 81-7.

Chiappa K H and Young R R (1985) Evoked responses. Overused, underused, or misused? *Archives of Neurology,* 42(1): 76-7.

Cohen, M. S., R Goldman, et al. (2001). Simultaneous EEG and fMRI Made Easy. Organization for Human Brain Mapping, Brighton, UK.

Cohen M S (1997) Parametric analysis of fMRI data using linear systems methods. *Neuroimage;* 6(2): 93-103.

Cohen M S and Bookheimer S Y (1994) Localization of brain function using magnetic resonance imaging. *Trends in Neuroscience;* 17(7): 268-77.

Cohen M S and Britt R H (1982) Effects of sodium pentobarbital, ketamine, halothane, and chloralose on brainstem auditory evoked responses. *Anesthesia and Analgesia;* 61(4): 338-43.

Cohen M S and DuBois R M (1999) Stability, repeatability, and the expression of signal magnitude in functional magnetic resonance imaging. *Journal of Magnetic Resonance Imaging;* 10(1): 33-40.

Cohen M S, Kelley D A, Rohan M L and Roemer P A. (1996) An MR instrument optimized for intracranial neuroimaging [abstract]. Human Brain Mapping 96 1996; P1A1-007. Boston, Mass.

Davidson R J (1988) EEG measures of cerebral asymmetry: conceptual and methodological issues. *International Journal of Neuroscience,* 39(1-2): 71-89.

Davidson R J, Schaffer C E and Saron C (1985) Effects of lateralized presentations of faces on self-reports of emotion and EEG asymmetry in depressed and non-depressed subjects. *Psychophysiology;* 22(3): 353-64.

Ekman P, Davidson R J and Friesen W V (1990) The Duchenne smile: emotional expression and brain physiology. II. *J Pers Soc Psychol;* 58(2): 342-53.

Engel J, Jr. (1984) A practical guide for routine EEG studies in epilepsy. *Journal of Clinical Neurophysiology;* 1(2): 109-42.

Engel J, Jr. (2000) Overview of functional neuroimaging in epilepsy [In Process Citation]. *Advances in Neurology;* 83: 1-9.

Fishbein D H, Herning R I, Pickworth W B, Haertzen C A, Hickey J E and Jaffe J H (1989) EEG and brainstem auditory response potentials in adult male drug abusers with self-reported histories of aggressive behavior. Biological Psychiatry, 26(6): 595-611.

Goldie W D, Chiappa K H, Young R R and Brooks E B (1981) Brainstem auditory and short-latency somatosensory evoked responses in brain death. *Neurology,* 31(3): 248-56.

Goldman R, Cohen M, Engel J and Stern J. (2000) Combining EEG and functional MRI: Cleaning up the electrical signals [abstract]. International Society for Magnetic Resonance in Medicine Eighth annual meeting 2000; Denver.

Goldman R, Stern J, Engel J and Cohen M (2000) Acquiring Simultaneous EEG and Functional MRI. *Clinical Neurophysiology,* 11: tbd.

Goldman, R, M. S. Cohen, et al. (2001). Tomographic Mapping of Alpha Rhythm Using Simultaneous EEG/fMRI. Organization for Human Brain Mapping, Brighton, UK.

Hennig J and Hodapp M (1993) BURST imaging. *MAGMA;* 1: 39-48.

Henry T R, Sutherling W W, Engel J J, Risinger M W, Levesque M F, Mazziotta J C, et al. (1991) Interictal cerebral metabolism in partial epilepsies of neocortical origin. *Epilepsy Research,* 10(2-3): 174-82.

Hoffman A, Jager L, Werhahn K;, Jaschke M, Noachtar S and Reiser M (2000) Electroencephalography during functional echo-planar imaging: detection of epileptic spikes using post-processing methods [In Process Citation]. *Magnetic Resonance in Medicine,* 44(5): 791-8.

Horne j (2000) Neuroscience. Images of lost sleep [news; comment]. Nature, 403(6770): 605-6.

Ingvar, D. R., M. Baldy-Moulinier, et al. (1965). "Regional cerebral blood flow related to EEG." *Acta Neurol Scand Suppl* 14: 179-82.

Jackson G, Connelly A, Cross J, Gordon I and Gadian D (1994) Functional magnetic resonance imaging of focal seizures. *Neurology*, 44: 850-856.

Jones, B. E. (2000). Basic mechanisms of sleep-wake states. *Principles and practice of sleep medicine*. M. Kryger, T. Roth and W. DeMent. Philadelphia, W B Saunders: 134-154.

Klimesch W, Doppelmayr M, Russegger H, Pachinger T and Schwaiger J (1998) Induced alpha band power changes in the human EEG and attention. *Neurosci Lett;* 244(2): 73-6.

Krakow I, Woermann F G, Symms M R, Allen P J, Lemieux L, Barker G J, et al. (1999) EEG-triggered functional MRI of interictal epileptiform activity in patients with partial seizures. *Brain;* 122(Pt9): 1679-88.

Kwong K K, Belliveau J W, Chesler D A, Goldberg I E, Weisskoff R M, Poncelet B P, et al. (1992) Dynamic magnetic resonance imaging of human brain activity during primary sensory stimulation. *Proceedings of the National Academy of Science USA;* 89(12): 5675-9.

Lambert M V and Robertson M M (1999) Depression in epilepsy: etiology, phenomenology, and treatment *Epilepsia;* 40(Suppl 10): S21-47.

Lindgren K A, Larson C L, Schaefer S M, Abercrombie H C, Ward R T, Oakes T R, et al. (1999) Thalamic metabolic rate predicts EEG alpha power in healthy control subjects but not in depressed patients. *Biological Psychiatry;* 45(8): 943-52.

Loo S K, Teale P D and Reite M L (1999) EEG correlates of methylphenidate response among children with ADHD: a preliminary report. *Biological Psychiatry;* 45(12): 1657-60.

Lopes da Silva F H, Lierop T H v, Schrijer C F and Leeuwen W S v (1973) Organization of thalamic and cortical alpha rhythms: spectra and coherences. *Electroencephalography and Clinical Neurophysiology;* 35(6): 627-39.

Lopes da Silva F H, Vos J E, Mooibroek J and Van Rotterdam A (1980) Relative contributions of intracortical and thalamo-cortical processes in the generation of alpha rhythms, revealed by partial coherence analysis. *Electroencephalography and Clinical Neurophysiology;* 50(5-6): 449-56.

Lovblad K O, Thomas R, Jakob P M, Scammell T, Bassetti C, Griswold M, et al. (1999) Silent functional magnetic resonance imaging demonstrates focal activation in rapid eye movement sleep. *Neurology;* 53(9): 2193-5.

Lurito J T, Lowe M J, Sartorius C and Mathews V P (2000) Comparison of fMRI and intraoperative direct cortical stimulation in localization of receptive language areas. *J Comput Assist Tomogr,* 24(1): 99-105.

Madsen, P. L., S. Holm, et al. (1991). "Human regional cerebral blood flow during rapid-eye-movement sleep." *J Cereb Blood Flow Metab* 11(3): 502-7.

Madsen, P. L., J. F. Schmidt, et al. (1991). "Cerebral oxygen metabolism and cerebral blood flow in man during light sleep (stage 2)." *Brain Res* 557(1-2): 217-20.

Mannelli P, Janiri L, Tempesta E and Jones R T (1993) Prediction in drug abuse: cocaine interactions with alcohol and buprenorphine. *British Journal of Psychiatry Supplement;* (21): 39-45.

Maquet P (1999) Brain mechanisms of sleep: contribution of neuroimaging techniques. *J Psychopharmacol;* 13(4): S25-8.

Maquet P, Dive D, Salmon E, Sadzot B, Franco G, Poirrier R, et al. (1992) Cerebral glucose utilization during stage 2 sleep in man. *Brain Research;* 571(1): 149-53.

Maquet P, Dive D, Salmon E, Sadzot B, Franco G, Poirrier R, et al. (1990) Cerebral glucose utilization during sleep-wake cycle in man determined by positron emission tomography and [18F]2-fluoro-2-deoxy-D-glucose method. *Brain Research;* 513(1): 136-43.

Maquet P, Laureys S, Peigneux P, Fuchs S, Petiau C, Phillips C, et al. (2000) Experience-dependent changes in cerebral activation during human REM sleep. *Nat Neurosci;* 3(8): 831-6.

Maquet P, Peters J, Aerts J, Delfiore G, Degueldre C, Luxen A, et al. (1996) Functional neuroanatomy of human rapid-eye-movement sleep and dreaming. *Nature;* 383 (6596): 163-6.

Maquet P and Phillips C (1998) Functional brain imaging of human sleep. *J Sleep Res;* 7(Suppl 1): 42-7.

Markand O N (1984) Electroencephalography in diffuse encephalopathies. *Journal of Clinical Neurophysiology;* 1(4): 357-407.

Maykut M O (1985) Health consequences of acute and chronic marihuana use. *Progress in Neuropsychopharmacoloy and Biological Psychiatry,* 9(3): 209-38.

McNamara J O (1994) Cellular and molecular basis of epilepsy. *Journal of Neuroscience;* 14(6): 3413-25.

Nofzinger, E. A., M. A. Mintun, et al. (1997). "Forebrain activation in REM sleep: an FDG PET study." *Brain Res* 770(1-2): 192-201.

Nofzinger, E. A., M. A. Mintun, et al. (1998). "A method for the assessment of the functional neuroanatomy of human sleep using FDG PET." *Brain Res Brain Res Protoc* 2(3): 191-8.

Ogawa S, Lee T M, Kay A R and Tank D W (1990a) Brain magnetic resonance imaging with contrast dependent on blood oxygenation. *Proceedings of the National Academy of Science USA;* 87(24): 9868-72.

Ogawa S, Lee T M, Nayak A S and Glynn P (1990b) Oxygenation-sensitive contrast in magnetic resonance image of rodent brain at high magnetic fields. *Magnetic Resonance in Medicine,* 14(1): 68-78.

Ogawa S, Tank D W, Menon R, Ellermann J M, Kim S G, Merkle H, et al. (1992) Intrinsic signal changes accompanying sensory stimulation: functional brain mapping with magnetic resonance imaging. *Proceedings of the National Academy of Science USA;* 89(13): 5951-5.

Patel M R, Blum A, Pearlman J D, Yousuf N, Ives J R, Saeteng S, et al. (1999) Echo-planar functional MR imaging of epilepsy with concurrent EEG monitoring. *American Journal of Neuroradiology;* 20(10): 1916-9.

Petersen I and Eeg-Olofsson O (1971) The development of the electroencephalogram in normal children from the age of 1 through 15 years. Non-paroxysmal activity. *Neuropadiatrie;* 2(3): 247-304.

Pfurtscheller G and Aranibar A (1977) Event-related cortical desynchronization detected by power measurements of scalp EEG. *Electroencephalography and Clinical Neurophysiology;* 42(6): 817-26.

Press W, Vetterling W, Teukolsky S and Flannery B (1992) *Numerical Recipes in C—The Art of Scientific Computing.* Cambridge:Cambridge University Press.

Ramabhadran B, Frost J D, Jr., Glover J R and Ktonas P Y (1999) An automated system for epileptogenic focus localization in the electroencephalogram. *Journal of Clinical Neurophysiology;* 16(1): 59-68.

Rechtschaffen A and Kales A (1968), Ed.^Eds. *A manual of standardized terminology, techniques and scoring system for sleep stages of human subjects.* Bethesda, Md.: U.S. Dept of Health, Education, and Welfare.

Reese T, Davis T and Weisskoff R (1995) Automated shimming at 1.5 T using echo-planar image frequency maps. *Journal of Magnetic Resonance Imaging;* 5: 739-745.

Roux F E, Boulanouar K, Ranjeva J P, Tremoulet M, Henry P, Manelfe C, et al. (1999) Usefulness of motor functional MRI correlated to cortical mapping in Rolandic low-grade astrocytomas. *Acta Neurochir;* 141(1): 71-9.

Schomer D L, Bonmassar G, Lazeyras F, Seeck M, Blum A, Anami K, et al. (2000) EEG-Linked functional magnetic resonance imaging in epilepsy and cognitive neurophysiology. *Journal of Clinical Neurophysiology;* 17(1): 43-58.

Schulder M, Maldjian J A, Liu W C, Holodny A I, Kalnin A T, Mun I K, et al. (1998) Functional image-guided surgery of intracranial tumors located in or near the sensorimotor cortex. *Journal of Neurosurgery;* 89(3): 412-8.

Seeck M, Lazeyras F, Michel C M, Blanke O, Gericke C A, Ives J, et al. (1998) Non-invasive epileptic focus localization using EEG-triggered functional MRI and electromagnetic tomography. *Electroencephalography and Clinical Neurophysiology;* 106(6): 508-12.

Shagass C (1972) Electrical activity of the brain. In: *Handbook of psychophysiology, Edited by N. S. Greenfield and R. A. Sternbach. New York: Holt, Rinehart, & Winston, pp.* 263-328.

Starr A and Achor J (1978) The generators of the auditory brainstem potentials as revealed by brainstem lesions in both man and cat pp. 443-52. *In: Naunton R F, Fernandez C, ed. Evoked electrical activity in the auditory nervous system. New York, Academic Press,;:*

Stefan H, Schneider S, Abraham F K, Bauer J, Feistel H, Pawlik G, et al. (1990) Magnetic source localization in focal epilepsy. Multichannel magnetoencephalography correlated with magnetic resonance brain imaging. *Brain,:* 1347-59.

Symms M R, Allen P J, Woermann F G, Polizzi G, Krakow K, Barker G J, et al. (1999) Reproducible localization of interictal epileptiform discharges using EEG-triggered fMRI. *Phys Med Biol;* 44(7): N161-8.

Tokunaga I, Takeichi S, Kujime T and Maeiwa M (1989) Electroencephalographical analysis of acute drug intoxication—S S Bron solution—W. *Arukoru Yenkyuto Yakubutsu Izon;* 24(6): 471-9.

Warach S, Ives J R, Schlaug G, Patel M R, Darby D G, Thangaraj V, et al. (1996) EEG-triggered echo-planar functional MRI in epilepsy. *Neurology;* 47(1): 89-93.

Warach S, Levin J M, Schomer D L, Holman B L and Edelman R R (1994) Hyperperfusion of ictal seizure focus demonstrated by MR perfusion imaging. *American Journal of Neuroradiology;* 15(5): 965-8.

Wrobel A (2000) Beta activity: a carrier for visual attention. *Acta Neurobiol Exp;* 60(2): 247-60.

The foregoing description of preferred embodiments of the invention has been presented for the purposes of illustration and description. It is not intended to be exhaustive or to limit the invention to a precise form disclosed. Many modifications and variations are possible in light of the above teaching. It is intended that the scope of the invention be limited not by this detailed description, but rather by the claims appended hereto.

What is claimed is:

1. A method of reducing contamination of electrical signals recorded in the presence of repeated interference contamination comprising:

(a) obtaining an electrical signal, wherein the electrical signal was recorded in the presence of a contaminating signal;

(b) detecting a timing signal that occurs at a fixed time point during the electrical signal relative to the onset of the contaminating signal;

(c) digitizing the electrical signal, wherein the digitizing begins with the timing signal;

(d) analyzing a plurality of digitized electrical signals, wherein the electrical signals are synchronized with respect to the timing signal, to obtain an estimated contaminating signal; and (e) subtracting the estimated contaminating signal from the digitized electrical signal, thereby reducing contamination of the electrical signal;

wherein the analyzing to obtain the estimate of the contaminating signal comprises calculating a weighted average of the contaminating signals; and wherein the estimate of the contaminating signal is biased towards recent events, and comprises a first sum consisting of the nth electrical signal added to a scalar multiple, w, of a prior estimate of the contaminating signal, divided by a second sum obtained by adding a series $1+w2+w3+w4 \ldots + \ldots wn$.

2. The method of claim 1, wherein the electrical recording comprises an electrophysiological signal.

3. The method of claim 1, wherein the estimate of the contaminating signal is multiplied by a scalar prior to the subtracting of step (e).

4. The method of claim 2, wherein the electrophysiological signal comprises an electroencephalographic recording, an electromyelographic recording, an electrocardiographic recording or a measure of galvanic skin resistance.

5. The method of claim 1, wherein the interference comprises interference arising from inductively coupled magnetic fields.

6. The method of claim 1, wherein the interference comprises interference arising from alternating current (AC) line noise.

7. A method of reducing contamination of electrical signals recorded in the presence of repeated interference contamination comprising:

(a) obtaining an electrical signal, wherein the electrical signal was recorded in the presence of a contaminating signal;

(b) detecting a timing signal that occurs at a fixed time point during the electrical signal relative to the onset of the contaminating signal;

(c) digitizing the electrical signal, wherein the digitizing begins with the timing signal;

(d) analyzing a plurality of digitized electrical signals, wherein the electrical signals are synchronized with respect to the timing signal, to obtain an estimated contaminating signal; and (e) subtracting the estimated contaminating signal from the digitized electrical signal, thereby reducing contamination of the electrical signal, wherein the digitizing is performed at a sampling rate below the Nyquist rate for the contaminating signal.

8. The method of claim 1, wherein the electrical signal obtained in step (a) is passed through a low pass filter prior to the digitizing, at a frequency of approximately one half of the frequency at which the electrical signal is sampled.

9. The method of claim 8, wherein the low pass filter passes signal frequencies of less than about 200 Hz.

10. The method of claim 1, wherein the method is performed concurrently with Magnetic Resonance Imaging of the subject.

11. The method of claim 10, wherein the electrical signal comprises an electrophysiological signal and the contaminating signal comprises gradient activity.

12. The method of claim 11, wherein the electrical signal comprises an electrophysiological signal and the contaminating signal comprises radio frequency transmitter activity.

13. The method of claim 1, wherein the digitizing is performed at a rate of about 200 to about 5000 samples per second.

14. A method of reducing contamination of electrical signals recorded in the presence of repeated interference contamination comprising:
  (a) obtaining an electrical signal and removing a DC offset from the electrical signal by analog subtraction using a differential amplifier, wherein the electrical signal was recorded in the presence of a contaminating signal;
  (b) detecting a timing signal that occurs at a fixed time point during the electrical signal relative to the onset of the contaminating signal;
  (c) digitizing the electrical signal, wherein the digitizing begins with the timing signal;
  (d) analyzing a plurality of digitized electrical signals, wherein the electrical signals are synchronized with respect to the timing signal, to obtain an estimated contaminating signal; and
  (e) subtracting the estimated contaminating signal from the digitized electrical signal. thereby reducing contamination of the electrical signal,
wherein the DC offset is measured:
  (i) by analog to digital conversion, and averaged over a time period long compared to lowest frequencies of interest in the electrical signal; or
  (ii) in an analog integrator having a time constant long compared with lowest freguencies of interest in the signal.

15. The method of claim 14, wherein the time period of (i) is approximately 10 times longer than the lowest frequencies of interest in the electrical signal.

16. The method of claim 14, wherein the analog subtraction comprises converting the averaged signal to an analog voltage and electrically subtracting the averaged signal from the electrical signal through differential amplification.

17. The method of claim 14, wherein the time constant of (ii) is approximately 10 times the lowest frequencies of interest.

18. The method of claim 2, wherein the electrophysiological recording comprises an electroencephalogram and is recorded concurrently with magnetic resonance image acquisition.

19. The method of claim 18, wherein the electrophysiological recordings are used to inform interpretations of the magnetic resonance images.

20. A method of reducing contamination of electrical signals recorded in the presence of repeated interference contamination comprising:
  (a) obtaining an electrical signal, wherein the electrical signal was recorded in the presence of a contaminating signal;
  (b) detecting a timing signal that occurs at a fixed time point during the electrical signal relative to the onset of the contaminating signal;
  (c) digitizing the electrical signal, wherein the digitizing begins with the timing signal;
  (d) analyzing a plurality of digitized electrical signals, wherein the electrical signals are synchronized with respect to the timing signal, to obtain an estimated contaminating signal;
  (e) subtracting the estimated contaminating signal from the digitized electrical signal, thereby reducing contamination of the electrical signal;
wherein the estimate of the contaminating signal is multiplied by a scalar prior to the subtracting of step (e); wherein the electrical recording comprises an electrophysiological signal and wherein the electrophysiological recordings comprise an electroencephalogram, are recorded concurrently with magnetic resonance image acquisition, and are used in a statistical analysis of change in intensity of the magnetic resonance signal.

21. The method of claim 20, further comprising determining a correlation between change in intensity of the magnetic resonance signal and a feature of the electrophysiological recording.

22. The method of claim 21, wherein the correlation is used to make statistical images that represent an association between the electrical signals and the intensity of the magnetic resonance signal intensity.

23. The method of claim 21, wherein the feature of the electrophysiological recording comprises a time course of signal intensity change in defined frequency bands contained in the electrophysiological recording.

24. The method of claim 23, wherein the defined frequency bands correspond to standard ranges used for clinical interpretations of the electroencephalogram.

25. The method of claim 24, wherein the standard ranges are selected from the group consisting of from 0 to approximately 4 Hz (the Delta band), from approximately 4 to approximately 8 Hz (the Theta band), from approximately 8 to approximately 12 Hz (the Alpha band), from approximately 12 to approximately 30 Hz (the Beta band), and from approximately 30 Hz and greater (the Gamma band).

26. The method of claim 18, further comprising convolving the time course of the electrophysiological signal with an estimate of the magnetic resonance hemodynamic impulse response function.

27. The method of claim 2, wherein the electrophysiological recording comprises an electroencephalographic recording.

28. The method of claim 2, wherein the method is performed concurrently with Magnetic Resonance Imaging of the subject.

29. The method of claim 7, wherein the electrical recording comprises an electrophysiological signal.

30. The method of claim 29, wherein the electrophysiological recording comprises an electroencephalographic recording.

31. The method of claim 30, wherein the method is performed concurrently with Magnetic Resonance Imaging of the subject.

32. The method of claim 14, wherein the electrical recording comprises an electrophysiological signal.

33. The method of claim 32, wherein the electrophysiological recording comprises an electroencephalographic recording.

34. The method of claim 33, wherein the method is performed concurrently with Magnetic Resonance Imaging of the subject.

* * * * *